(12) United States Patent
Chow et al.

(10) Patent No.: US 6,500,323 B1
(45) Date of Patent: Dec. 31, 2002

(54) METHODS AND SOFTWARE FOR DESIGNING MICROFLUIDIC DEVICES

(75) Inventors: Andrea W. Chow, Los Altos, CA (US); Anne R. Kopf-Sill, Portola Valley, CA (US); Calvin Y. H. Chow, Portola Valley, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/277,367

(22) Filed: Mar. 26, 1999

(51) Int. Cl.[7] .......................... G01N 27/447; B01L 3/00
(52) U.S. Cl. ........................ 204/450; 204/453; 422/100
(58) Field of Search .................................. 204/450, 451, 204/454, 453, 600, 601, 602, 604; 422/70, 99, 100; 702/19, 22

(56) References Cited

U.S. PATENT DOCUMENTS

| | | |
|---|---|---|
| 4,390,403 A | 6/1983 | Batchelder |
| 4,908,112 A | 3/1990 | Pace |
| 5,126,022 A | 6/1992 | Soane et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,699,157 A | 12/1997 | Parce |
| 5,750,015 A | 5/1998 | Soane et al. |
| 5,779,868 A | 7/1998 | Parce et al. |
| 5,800,690 A | 9/1998 | Chow et al. |
| 5,842,787 A | 12/1998 | Kopf-Sill et al. |
| 5,846,727 A | * 12/1998 | Soper et al. ................. 435/6 |
| 5,852,495 A | 12/1998 | Parce |
| 5,858,804 A | * 1/1999 | Zanzucchi et al. .......... 436/536 |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,942,443 A | 8/1999 | Parce et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |

(List continued on next page.)

FOREIGN PATENT DOCUMENTS

| | | |
|---|---|---|
| WO | WO9604547 | 2/1996 |
| WO | WO9702357 | 1/1997 |
| WO | WO9800705 | 1/1998 |
| WO | WO9912016 | 3/1999 |

OTHER PUBLICATIONS

Culbertson et al. ("Dispersion Sources for Compact Geometries on Microchips", Anal. Chem. 1998, 70, 3781–3789), Sep. 1998.*

(List continued on next page.)

*Primary Examiner*—Jill Warden
*Assistant Examiner*—Ab Noguerola
(74) *Attorney, Agent, or Firm*—Matthew B. Murphy; Andrew L. Filler

(57) ABSTRACT

Methods and systems for designing optimized fluidic channel networks for performing different analytical operations, which include the steps of selecting a driving force, identifying at least a first reaction parameter, and designing the channel network by determining channel lengths and cross-sectional dimensions that are optimized for the reaction requirements in view of the selected driving force. Preferred methods are used to design integrated microscale fluidic systems.

23 Claims, 14 Drawing Sheets

U.S. PATENT DOCUMENTS

| | | | |
|---|---|---|---|
| 5,965,410 A | 10/1999 | Chow et al. | |
| 5,972,187 A | 10/1999 | Parce et al. | |
| 5,976,336 A | 11/1999 | Dubrow et al. | |
| 5,989,402 A | 11/1999 | Chow et al. | |
| 6,001,231 A | 12/1999 | Kopf-Sill | |
| 6,004,515 A | 12/1999 | Parce et al. | |
| 6,011,252 A | 1/2000 | Jensen | |
| 6,012,902 A | 1/2000 | Parce | |
| 6,062,261 A | * 5/2000 | Jacobson et al. | 137/827 |
| 6,136,272 A | * 10/2000 | Weigl et al. | 422/82.05 |

OTHER PUBLICATIONS

Papautsky et al. ("Microchannel fluid behavior using micropolar fluid theory", Proc. IEEE Annu. Int. Workshop Micro Electro Mech. Syst., 11th, 544–549, 1998), 1998.*

Shoji et al. ("Mrcroflow devices and systems", J. Micromech. Microeng. 4 (Sep. 1994) 157–171), Sep. 1998.* pp. 115–117 of "A Dictionary of Electrochemistry", Davies et al., John Wiley & Sons, 1976.*

Mastrangelo, C.H. et al., "Microfabricated Devices for Genetic Diagnostics", *Proc. of IEEE* (1998) 86(8):17691787.

Shoji, S. et al., "Microflow devices and systems", *J. Micromech. Microeng.* (1994) 4:157–171.

Aris, R. "ON The dispersion of a solute in a fluid flowing through a tube," *Proc. Roy. Soc. London* (1956) A235:67–77.

Chatwin, P.C. et al., "The effect of aspect ratio on longitudinal diffusivity in rectangular channels," *J. Fluid Mech.* (1982) 120:347–358.

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798.

Doshi, M.R. et al., "Three Dimensional Laminar Dispersion in Open and Closed Rectangular Conduits," *Chem. Eng. Sci.* (1978) 33:795–804.

Guell, D.C. et al., "Taylor Dispersion in Conduits of Large Aspect Ratio," *Chem. Eng. Comm.* (1987) 58:231–244.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Taylor, G. et al., "Dispersion of soluble matter in solvent flowing slowly through a tube," *Proc. Roy. Soc. London* (1953) 219A:186–203.

* cited by examiner

METHODS AND SOFTWARE FOR DESIGNING MICROFLUIDIC DEVICES

BACKGROUND OF THE INVENTION

Microfluidic devices have gained interest as a potential avenue for increasing throughput, accuracy and automatability of chemical, biochemical and biological analyses while reducing instrument and reagent costs, space requirements, and the like. Typically, such systems employ integrated channel networks disposed in solid substrates. Analytical reagents are transported through the conduits, mixed, diluted, separated and analyzed. In their simplest forms, such channel networks merely require a network of conduits connecting the various reagent and or sample sources, as well as a material transport system for moving the various reagents through those conduits in a controlled fashion. Specifically, all that is required for basic, rudimentary function are sources of reagents, a fluid connection between those sources, a means for controllably moving those reagents together via that fluid connection, and a detection or analysis system for analyzing those reagents.

While the design and operation of many microfluidic devices and systems can appear elegant in its simplicity, in order to maximize their benefit, these devices and systems should be optimized for the particular analytical operation for which they are intended. Specifically, mere fabrication of interconnected channels into a substrate may provide one with an ability to perform a desired operation, e.g., reaction or separation. However, that operation is more than likely to be running under sub-optimal conditions. In particular, most channel network design to date in microfluidics has simply focused upon getting a reagent from a first location to a second location without analyzing and/or optimizing for how that transport is carried out.

As can be seen from the foregoing, there exists a profound need for methods for designing microfluidic channel networks, which methods optimize for the analytical operation that is to be carried out. The present invention meets these and a variety of other needs.

SUMMARY OF THE INVENTION

In a first aspect, the present invention provides a method of designing a channel network for a microfluidic device for performing a given analysis. The method comprises selecting a driving force for moving fluid materials through said microfluidic device. At least one reaction is identified for the given analysis. A channel network is designed that performs the given analysis using the driving force. The channel network comprises at least first, second and third channel segments. The second and third channel segments intersect and are in fluid communication with the first channel segment. The designing comprises providing first, second and third lengths for the first, second and third channel segments, respectively, and at least a first cross-sectional dimension for each of the first, second and third channel segments. The first, second and third lengths and at least one cross-sectional dimension are substantially optimized for the at least one reaction requirement.

A further aspect of the present invention is a method of designing a channel network for a microfluidic device for performing a given analysis. At least first, second and third parameters of said analysis are identified. A driving force is selected for moving fluid reagents through the channel network for performing the analysis. A channel network is then designed for use with the driving force to perform the given analysis while operating within the first, second, and third parameters.

Another aspect of the present invention is a computer implemented process for designing channel networks for performing a desired analytical operation. A selected driving force is input into a computer to be used in performing the analytical operation of at least one reaction requirement. The computer comprises appropriate programming for calculating first, second and third lengths for first, second and third interconnected channel segments, and at least one cross-sectional dimension of the first, second and third channel segments. The first, second and third lengths and the at least one cross-sectional dimension are substantially optimized for the at least one reaction requirement in performing the analytical operation.

DETAILED DESCRIPTION OF THE INVENTION

I. General Methods

Figure 1A:
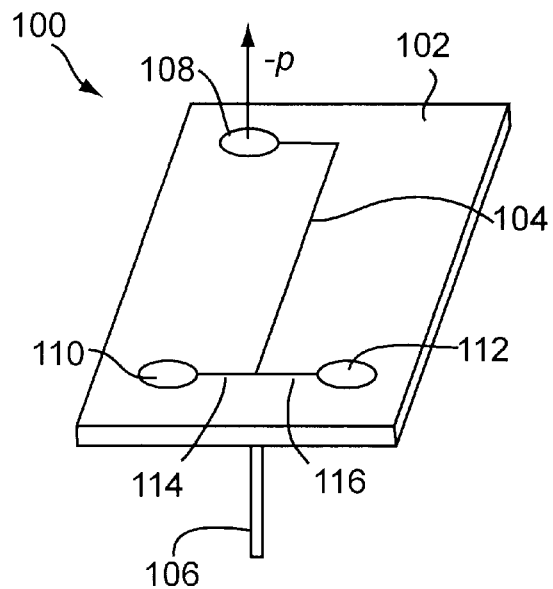
FIG. 1A is a schematic illustration of a perspective view of a microfluidic device incorporating the channel network, while FIG. 1B schematically illustrates a "circuit" diagram for the channel network.

As noted previously, microfluidic devices and systems have been employed in the performance of a variety of different operations, including high and low throughput screening assays and macromolecular characterization operations, e.g., size-based separations and sequencing reactions.

Typically, the fabrication of microfluidic channel networks has only considered one or two factors when laying out the design of the channel network. In fact, general channel network design has involved only consideration of the starting point and ending point of the material that is to be transported through the channel network, and the insertion of a channel connecting the two points. More advanced methods of designing such channel networks also take into consideration factors such as the amount of occupied substrate space, the distance of sample wells from an analysis channel, and the like (See e.g., Published International Application No. WO 98/49548, which is incorporated herein by reference in its entirety for all purposes). While these factors are important, they are all related to the two-dimensional space occupied by the channel network, e.g., across the surface of a given substrate.

Despite the consideration of these factors, there remain a number of additional factors that each could be considered and optimized, when designing microfluidic channel networks including, e.g., channel geometry, fluid transport methods, reagent characteristics including fluid properties and structure/fluid interactions, and requirements of a desired reaction that is to be carried out within the channel network. The present invention generally provides methods of designing microfluidic devices that take these additional factors into consideration in the design of optimized microfluidic channel networks, which in turn are used in efficient analytical and/or synthetic operations. For example, in at least a first respect, the present invention provides a method of designing a channel network for a microfluidic device for performing a given analysis.

As a first step, the methods of the invention involve selection of the particular driving force that is used with the device. By "driving force" is meant the method or system which causes the movement of fluids or other materials through the particular microfluidic channel network that is being designed. In particularly preferred aspects, the driving force is selected from pressure-based fluid transport systems, electrokinetic fluid transport systems, and hybrids of the two. The nature of the driving force can have profound implications on the movement of fluids through the microfluidic channel network.

As an additional step, the methods of the invention also comprise the identification of at least two reaction requirements for the particular analysis for which the device is intended. By "reaction requirements" is generally meant one or more parameters that affects the outcome of the reaction regardless of where or how that reaction is carried out. Such reaction parameters include, e.g., reagent characteristics, reagent concentrations, reaction temperatures, reaction times, ratios of reagents, and the like.

In a further step, the methods comprise actually designing a channel network that performs the given analysis using the selected driving force, and practices the reaction requirements for the particular desired analysis. In a channel network that includes at least first, second and third channel segments, the designing step involves providing first, second and third lengths for the first, second and third channel segments, respectively. In providing the channel segment lengths and cross-sectional dimensions used to optimize the desired operation, the methods described herein typically take account of a number of additional parameters, such as the fluid mechanics of the fluid reagents within the system, as well as practical requirements of the overall system. A variety of specific considerations are set forth in greater detail, below.

The lengths of these channel segments are optimized for the particular reaction that is to be performed, based upon the chosen reaction requirements, e.g., the dilution factor for the reagents, the overall reaction time, or the like, and taking into account the above-noted considerations.

As used herein, "optimization" refers to the improvement of desired results of a given operation to a maximal extent permitted by the required or critical conditions under which the operation is performed. In some cases further improvement may be possible under different conditions that are not practical or available under the conditions of the operation at a given time. As such, the incremental improvement provided under the existing conditions would constitute optimization of the system.

The designing step also includes optimization of at least a first cross-sectional dimension for each of the first, second and third channel segments, for the particular selected reaction requirement. In particular, depending upon the selected reaction requirement, the width and/or depth of the channels in the network can affect the material flowing through the channel.

II. Selection of Driving Force

Initially, in setting out to design a microfluidic system for performing a particular assay, one must first select how the materials will be moved through the microfluidic channel network in order to mix, dilute, separate and/or detect the results of the assay. Selection of a particular driving force may be relatively inconsequential in certain assays. However, in a number of cases, the driving force selection is a critical parameter in the design of the assay and the microfluidic channel network. Typically, driving force for microfluidic systems is selected from pressure-based fluid transport, e.g., external pressure/vacuum sources or internal pumps, electrokinetic material transport systems, e.g., where fluid flow is driven by electric fields, or hybrids of the two, e.g., where the materials are driven partly by pressure based flow and partly electrokinetically.

One example of a driving force includes pressure-based fluid transport systems. Pressure-based systems typically utilize an external pressure source which forces material through the channels of the network by producing a pressure differential across the length of a particular channel segment through which material flow is desired. This is typically accomplished by applying a positive or negative pressure to one end of the particular channel segment in order to push or draw material through that channel segment. In a simple aspect, application of pressures is carried out by coupling a pressure source to a port that is disposed at one terminus of a particular channel segment to impart the pressure to the channel segment. Such pressure sources typically include pressure or vacuum pumps, or other pressure of vacuum sources. Alternatively, application of pressures may be carried out through the incorporation within the channel network of miniature pumps, e.g., electroosmotic pressure pumps as described in International Patent Application No. PCT/US98/20195, incorporated herein by reference in its entirety for all purposes. Such pumps are capable of generating the desired positive or negative pressures within channel segments that are connected to the pumps. Generally, pressure-based driving forces are preferred as they are generally the simplest to operate, and have the least effect on the fluids flowing through the channels of the system. Wicking systems which rely upon the incorporation of porous wicking materials at one or more termini of the channel(s) of the system are also useful to draw fluids through the channels of the system. Similarly, wicking-like systems that rely upon structures which have substantial capillarity are also particularly useful. Such systems are generally described in U.S. patent application Ser. No. 09/245,627, filed Feb. 5, 1999, and incorporated herein by reference.

Another example of driving force includes electrokinetic material transport. Generally, electrokinetic material transport systems provide for material movement, through the application of an electric field across the length of a channel segment through which fluid movement is desired. Such electrokinetic material transport and direction systems may include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure, which results from the application of an electric field across such structures. In brief, when a fluid is placed into a channel which has a surface bearing charged functional groups, e.g., hydroxyl groups in etched glass channels or glass microcapillaries, or surface charges in polymeric substrates, those groups can ionize. In the case of hydroxyl functional groups, this ionization, e.g., at neutral pH, results in the release of protons from the surface and into the fluid, creating a concentration of protons near the fluid/surface interface, or a positively charged "sheath" surrounding the bulk fluid in the channel. Application of a voltage gradient across the length of the channel, causes the proton sheath to move in the direction of the voltage drop, i.e., toward the negative electrode, and dragging the surrounded fluid with it. Use of electrokinetic forces to move fluids or materials contained therein in a controlled fashion and systems for carrying this out are described in detail in, e.g., U.S. Pat. Nos. 5,800,690 and 5,779,868, each of which is incorporated herein by reference.

The selection of a particular method or system for moving fluid or other materials through a microfluidic channel network can have major implications on how that fluid behaves within the channel network. For example, electrokinetic material transport systems the action of the electric fields on the fluids within the channels can have major effects on the flowing of those fluids. For example, in performing serial additions of materials within microfluidic channels, it is often desirable to incorporate spacer fluids between the serially introduced volumes of test fluid, in order to maintain separation of these test fluids. In order to prevent electrophoretic smearing of the materials in the test fluids, the spacer fluids are generally provided at much lower ionic strengths than the test fluid.

Where reagents for the desired assay are not highly charged, are contained by the spacer plugs, or features of electrokinetic transport are desired for the particular analysis, an electrokinetic material transport system can be selected as the driving force. For example, in some cases, it is desirable to take advantage of the electrophoretic effects that can result from the application of electric fields across channels containing reagent plugs. Specifically, where a reaction generates a product that is differently charged than the original reactants or substrates, the differential electrophoretic mobility of that product is used in an electrokinetic system, to separate the product from the substrate. In many cases, this permits the simple detection of the produce, even though the generation of the product is not accompanied by its own detectable signal.

Alternatively, a hybrid driving force may be used which combines the benefits of pressure-based fluid transport, e.g., lack of electrophoretic biasing, with the benefits of electrokinetic fluid transport, e.g., precise, solid state controllability. Such hybrid systems typically provide an electroosmotic flow system in only a portion of the channel network, where the electroosmotic flow system generates pressures in other parts of the network, without applying electric fields across the other parts of the network. Examples of these electroosmotic pressure pumps are described in, e.g., International Patent Application PCT/US98/20195. Briefly, by generating electroosmotic flow in one channel segment, one can create a pressure differential in an attached channel segment, either positive or negative, despite the fact that no electric field is applied across the attached channel segment. Depending upon the direction of electroosmotic flow in the pumping channel relative to the attached channel segment, the pressure may be positive or negative in the attached channel segment. In preferred aspects, a negative pressure is created at a downstream point in the attached channel segment, in order to avoid exposing any of the pre-reaction reagents or buffers to electric fields.

While these hybrid systems are operated by applied electric fields, the nature of the material flow of interest, through the channel network, is pressure-based, and thus the principles of channel design which are considered for pressure based systems are applicable here as well.

The selected driving force can have substantial effects on how material is moved through the channels of the device. For example, in systems which employ pressure-based material transport, all interconnected channels of the system are affected by pressure in one channel. As such, it is difficult to produce differential rates of flow in different interconnected channels under the same applied pressures without taking account of this in the channel design phase. Specifically, by varying the depth and or length of channels, one can affect the rate at which fluids flow through that channel under a given applied pressure or vacuum. Alternatively, channel networks can be designed to include partitions, e.g., valves, between channels.

Electrokinetic driving forces, because of their use of applied electric fields, can also have substantial effects on how fluids or other materials are moved through the channels of a microfluidic device. For example, in many analytical operations or assays, a number of the reagents and/or products can be highly charged. As a result, use of these reagents in microfluidic channel networks that utilize electrokinetic driving forces typically suffer from electrophoretic biasing of these charged reagents and/or products, e.g., where the reagents and/or products migrate much more rapidly or much more slowly than the fluid surrounding them. These biasing problems have been described in detail in, e.g., U.S. Pat. No. 5,779,868, which is incorporated herein by reference. Because this biasing can cause a number of difficulties, in such cases, it will often be desirable to select a non-electrophoretic method of transporting materials through the channel network, and particularly, a pressure based method of driving materials through the channel network, as described above.

Alternatively, steps can be taken to minimize and/or counteract this biasing. In designing channel networks, such biasing effects can be taken into account in the channel design themselves, e.g., by incorporating mixing regions or by minimizing distances across which material must be transported, thereby minimizing such biasing. Alternately, and typically, channels are designed to accommodate other methods of correcting for such biasing. Specifically, typically, electrophoretic biasing of individual and discrete material plugs is minimized through the inclusion of lower ionic strength separation or spacer fluids between the material plugs, which are typically in higher ionic strength buffers. However, such mixed fluid streams also have pressure variations over the length of the different fluid regions, resulting from the varied electroosmotic flow rates. These pressure differentials can adversely affect fluid flow at the intersection with other channels. However, by making the intersecting channel shallower, one can effectively counteract these pressure effects (see published International Patent Application No. WO 98/00705, which is incorporated herein by reference).

A number of additional criteria for the design of a microfluidic channel network need to be considered when one has selected an electrokinetic material transport system. For example, the nature of the fluid or buffer used in the system, e.g., its ionic strength, is directly related to the resistance or conductivity of the fluid, and thus directly affects the application of electric fields across them. Similarly, in mixed buffer systems, e.g., those using the high and low ionic strength fluid plugs to mitigate electrophoretic biasing of sample materials as described above, give rise to changes in the conductivity of the fluid filled channel, as a whole. Further, the entry and exit of fluid plugs from a particular channel segment produces variations in that conductivity depending upon the quantity of high salt fluid versus low salt fluid within a given channel at a given time. Of course, the amount of current passing through a given channel is directly proportional to the rate at which fluids or other materials are electrokinetically transported through the channel. Similarly, the level of resistance through a channel is also proportional to the amount of resistive heating that is generated in the channel. Reduction of such heating, or at least its adverse effects can be accomplished by designing channels that have relatively high surface area, e.g., wall area, to volume ratios, such that the substrate is a sufficiently large heat sink for the channel so as to dissipate any generated heat.

III. Selection/Identification of Analysis Requirements/ Reaction Parameters

In addition to selecting a preferred driving force for a given microfluidic operation, it is generally desirable to identify the analysis requirements, also termed "reaction parameters," that will affect or be affected by the design of a microfluidic channel network. Examples of parameters that have the greatest effect on and/or are most affected by channel network design, include those that are directly affected by the structure of the channel, such as its length, width or overall volume. These include, e.g., reaction times, reagent concentrations, reagent volumes, in the case of serial sample introduction systems, system throughput, and in the case of separation operations, e.g., CE methods, resolution of the separation, and in some cases, reaction temperatures and temperature profiles.

Reaction times are generally affected by the length of the channel in which the reaction is taking place and/or the flow rate of the reagents through that channel segment, before a subsequent operation step is performed, e.g., detection, separation or subsequent reaction. For example, where two interacting reagents are co-introduced into a reaction channel, they will flow along the reaction channel until they are detected, separated, or further reacted. While flow rates can dictate the amount of time, which these reagents are allowed to interact, in many cases, it is simpler to do this by adjusting the length of the reaction channel instead of or in addition to adjusting the flow rate.

Reagent concentrations are also dictated, at least in part, by the nature of the channel network in which the desired reaction/operation is being carried out. For example, by adjusting the ratio of the cross-section dimensions of two channels that meet at an intersection, in many cases, e.g., in pressure based flow systems, fixed voltage electrokinetic flow systems (as opposed to fixed current electrokinetic flow systems), one can dictate the ratio of flow coming from each channel, and thus, the concentration or mixture ratio of reagents coming from these two channels.

In addition to the foregoing, reagent volumes can also be a factor, which dictates channel network design factors. For example, where one requires a certain volume of material to be able to detect the results of a particular reaction, e.g., a fluorogenic reaction, channels may be provided with greater depths, at least at the detection portion of the channel. For example, where a reaction produces a fluorescent signal that is at or just below the detection limit of the detection system that is being used, one can provide the detection channel having twice the depth, and thereby double the volume of reagents that are being detected at a given time, thereby effectively doubling the amount of fluorescent signal that can be detected.

Similarly, the ability to detect a statistically significant signal is also often factored into the channel design, e.g., in cell based assays. Specifically, where the detected signal is obtained from discrete reaction components, e.g., cells, particles or beads, channels should be designed to provide for the detection of a statistically significant sampling of the cells, beads or particles, such that a significant analysis can be made. This may involve providing a channel of sufficiently narrow width to focus the particles at the detection point, or to pass a sufficiently large number of particles through the channel per unit time, such that a statistically significant number of particles may be interrogated in the allotted time frame.

Further, in performing cell-based assays in microfluidic systems, it is generally important to have channels with cross sectional dimensions that will accommodate cells without plugging. Accordingly, such channels typically have at least one cross-sectional dimension greater than about 10 $\mu$m, preferably greater than about 20 $\mu$m and more preferably greater than about 50 $\mu$m.

System throughput and reagent concentrations are also largely dictated by the structural configuration of the channel network. In addition to optimizing a channel network to simply accommodate the volume of material, which one desires to put through the system, there are other more complex concerns with respect to throughput. For example, the molecular diffusivity and/or dispersion of reagents may also comprise an important reaction parameter. In particular, the a rate at which different reagents diffuse within the reaction medium can have a profound effect on both the reagent concentration at any given point within the system, mixing rates of different components, as well as the rate at which serially introduced reagents can be introduced into the system without excessive or otherwise undesired intermixing of reagents, e.g., throughput. Again, dispersion of reagents within microfluidic channels is readily adjusted by adjusting the dimensions of the channel. Specifically, optimization of dispersion in channels based upon the cross-sectional dimension of the channels is described in, e.g., U.S. application Ser. No. 09/233,700, filed Jan. 19, 1999, which is incorporated herein by reference for all purposes.

As noted above, in some cases, the temperature at which a desired reaction is to take place, or a temperature profile at which a number of reactions are to take place can also dictate channel design parameters. For example, where an analytical operation involves a number of different reactions that take place at different temperatures, it may be desirable to physically isolate different regions of a channel network, in order to minimize temperature cross-overs from one region to another. Specifically, it may be desirable to provide a sufficient amount of substrate between two different temperature regions to insulate one from the other. In a more direct example, fluidic resistive heating of a channel's contents is directly related to the dimensions of a channel. Specifically, in certain aspects, it is desirable to heat a fluid in a channel by applying a current directly through that fluid. The amount of heat generated is directly related to the current applied and the resistance through the channel. The resistance of the channel is in turn, partially related to the cross-sectional dimensions of the channel. Examples of this type of temperature control are described in Published International Patent Application No. WO 99/12016, which is incorporated herein by reference for all purposes. Accordingly, optimization of channel dimensions may take into account the amount of current or power that one can safely and/or efficiently put through a given channel, in order to design channels having dimensions that are appropriate to yield adequate temperature control.

While it is generally a desirable pursuit to be able to optimize for all relevant parameters, it quickly becomes apparent that many of the more important parameters conflict with each other, whereby improving reaction conditions with respect to one parameter, detracts from reaction conditions with respect to another parameter. In such cases, optimization of such conflicting parameters typically involves a compromising optimization of both of the parameters rather than optimization of either one of the parameters to the detriment of the other. By way of example, increasing the cross sectional area of a channel may give rise to higher detection efficiencies, as described above. However, often such increases in cross-sectional area can have detrimental effects on the dispersion of materials in the channel, thereby reducing input or potentially adversely affecting reagent concentrations within discrete fluid regions within the channel. Similarly, while increasing reaction time, e.g., by lengthening a channel, may give rise to greater assay performance due to increased signal, at least in electrokinetic embodiments, such longer channels and longer transit times will likely give rise to greater levels of electrophoretic biasing.

IV. Designing the Channel Network

Once a driving force has been selected and the most important reaction requirements or parameters identified, one can set out designing the channel network which includes a structure that is optimized for the driving force and the selected reaction parameters, in accordance with the present invention.

The design process typically first identifies the factors that can or should be taken into account in producing an optimized channel network design for the given driving force and reaction requirements. There are a large number of different factors that should be considered in formulating the overall channel design. Typically, in accordance with the present invention, the structural characteristics of the channel network are dictated by factors that fall into the categories of practical or logistic factors (e.g., factors that are not directly concerned with the performance of the desired operation on the device, but are nonetheless important), fluid mechanics factors (e.g., the nature of the fluid used in the operation and how that fluid acts within the microfluidic environment), and structural factors, e.g., structures that may be required in the performance of a given operation, and which may affect the operation. Still further factors are dictated by the nature of the interactions between the microfluidic structure and the fluid materials placed into it.

A. Practical/Logistic Factors

As noted, in a first instance a number of practical considerations are typically taken into account when designing microfluidic channel networks. For example, in the case of many microfluidic channel networks, e.g., those used in performing high-throughput screening or assay operations, the channel network optionally includes an external sampling capillary which may or may not include the same cross-sectional dimensions of the remaining channels of the device. Other microfluidic channel networks on the other hand, are entirely integrated within a single body structure.

In addition, channel network design may take into consideration issues such as the cost of substrates and manufacturing those substrates. In particular, it is often desirable to minimize the area of a substrate that is occupied by a particular channel network, in order to minimize the substrate costs associated with the device's fabrication. Similarly, it is often desirable to group sample and reagent reservoirs to place like reservoirs in proximity to each other, e.g., to facilitate loading of the device. In each of these cases, there is a need for the channel network to conform to at least a general positioning of these wells/reservoirs, and for these reservoirs to be positioned as closely together as is practical, e.g., while allowing for access by typical fluid handling systems, e.g., pipettors and the like, and still permitting adequate space for the channel network. The amount of area occupied by a given channel network, also termed the "footprint," typically varies depending upon the application to which the network is to be put. In the case of multiplexed high-throughput channel networks, this footprint can be relatively large, e.g., between about 4 $cm^2$ and about 200 $cm^2$. Lower throughput systems, on the other hand typically have smaller footprints, e.g., between about 0.25 $cm^2$ to about 6 $cm^2$.

Similarly, reagent costs and/or availability may also dictate certain aspects of the design of a microfluidic device or system. For example, for high-cost reagents, sample wells may be provided having relatively small volumes. Of course, as noted above and described in greater detail below, the volume of the sample well can affect the influence of that well on fluid flow in any connected channel. Typically, the wells or reservoirs disposed in a microfluidic device's body structure are circular, having a diameter that is from about 1 mm to about 10 mm, and a depth of from about 2 mm to about 20 mm.

The overall robustness of a particular channel network is also generally taken into consideration in designing that channel network. Specifically, as these types of devices are generally intended for a wide range of different users of differing skill levels, it is generally desirable to make a particular channel network as forgiving as possible to misuse by the ultimate user. Thus, a range of tolerances is generally built into the design optimization process. Specifically, the optimization process typically selects the various parameters used to optimize the channel network as a range which varies about 50% on either side of a midpoint, e.g., an optimal reaction time may be from about 10 to about 30 seconds, 50% more or less than 20 seconds. Preferably, the tolerances will vary about 30% on either side of a midpoint, more preferably 20%, and still more preferably 10% on either side of a midpoint.

While the above-listed criteria generally have little or nothing to do with the actual analyses being carried out within the device, they are nonetheless important design features of the device, and should be considered in designing a channel network which still permits the carrying out of the particular analysis.

B. Fluid Mechanics Factors

Another set of factors that is generally taken into consideration in the design of microfluidic systems is the mechanics of fluid flow within microscale environments. Specifically, microscale channels and chambers, as well as reagent reservoirs or wells, can exert substantial capillary forces on fluids disposed therein. Such forces are often ignored in the fabrication of microfluidic channel networks, to the substantial detriment to the operation of such devices. Accordingly, in accordance with the design parameters of the present invention, these forces are identified and taken into account, particularly in conjunction with fluid transport parameters, which may be working against or in conjunction with these forces depending upon the direction of desired fluid flow.

By way of example, it can be seen that capillary forces that work against fluid flow in a desired direction can effectively slow that fluid flow. Furthermore, a slowed rate of fluid flow will have effects on a number of other parameters, e.g., reaction parameters such as reaction time, dispensed reagent volumes, etc. As such, in accordance with certain aspects of the present invention, many of these capillary forces are taken into account in the overall design of the channel network, either to minimize such forces or correct for those forces through the selection of an appropriate driving force, or through the selection of appropriate channel geometries.

Rates of dispersion of materials within microfluidic systems also affect the parameters of channel design, e.g., in the same manner as diffusion, described above. As used herein, the term "dispersion" refers to the convection-induced, longitudinal dispersion of material within a fluid medium due to velocity variations across streamlines, e.g., in pressure driven flow systems, electrokinetically driven flow systems around curves and corners, and electrokinetically driven flow systems having non-uniform buffer ionic concentrations, e.g., plugs of high and low salt solutions within the same channel system. For the purposes of the channel systems of the present invention, dispersion is generally defined as that due to the coupling between flow and molecular diffusion, i.e. Taylor dispersion. In this regime, the time-scale for dispersion due to convective transport is long or comparable to the time scale for molecular diffusion in the direction orthogonal to the flow direction. For discussions on dispersion and Taylor dispersion in particular, see, e.g., Taylor et al., Proc. Roy. Soc. London, (1953) 219A:186–203, Aris, Proc. Roy. Soc. London (1956) A235:67–77, Chatwin et al., J. Fluid mech. (1982) 120:347–358, Doshi et al., Chem. Eng. Sci. (1978) 33:795–804, and Guell et al., Chem. Eng. Comm. (1987) 58:231–244, each of which is incorporated herein by reference in its entirety for all purposes. Channel design optimization in light of dispersion and diffusion of serially introduced reagents is described in co-pending U.S. patent application Ser. No. 09/233,700, filed Jan. 19, 1999, which is incorporated herein by reference for all purposes.

Similarly, fluid viscosity also affects the rate at which fluids move through a channel network and is preferably taken into consideration in the design of the channel networks, in much the same manner as the capillary forces described above.

Other factors that may affect fluid flow, and particularly in electrokinetically driven systems, include, e.g., ionic strength of the fluids within the system (whether uniform or heterogeneous), pH of the fluids in the system, density, viscosity (aside from dispersion/diffusion issues described above), and the like.

In addition to the above, there are a number of more specific factors that are related to particular channel network configurations that are often taken into consideration. For example, in those systems employing an external capillary or pipettor element, it has been discovered that when the capillary element is withdrawn from a fluid source, a drop of fluid can remain at the open tip of the capillary. Further, the surface tension within this drop can be substantial, and often results in increase in the amount of pressure driving that drop into the capillary channel, resulting in increased flow rate until the surface tension is dissipated. Thus, in sampling multiple fluids, flow rates throughout the channel network are often seen to vary with the action of the pipettor channel.

The capillary forces yielded by the channels of the channel network, as well as those of the various wells and/or reservoirs associated with the channel network are also often taken into account when optimizing a channel network design. In particular, the corners at the base of a reservoir can exhibit substantial capillary forces on fluids within a channel that communicates with that well or reservoir, and as a result, affect fluid flow rates within those channels. Accordingly, such capillary forces may be countered or exploited in the channel network design, depending upon the desired operation to be performed by the system.

In a similar fashion, the depth or height of the wells can have an effect on the fluid flow within the system by providing a greater capacity for hydrostatic pressure, e.g., deeper wells can be used to provide greater fluid depths to drive fluid flow. Specifically, deeper narrower wells have a greater capacity to translate fluid volume into hydrostatic pressure than do shallower wider wells. Thus, depending upon the desirability or lack thereof for such hydrostatic pressure, one may factor in well diameter and depth into the optimization equation. Although generally described as circular wells having a diameter, it will be appreciated that wells may take virtually any shape, including, e.g., square, rectangular, hexagonal, octagonal, elliptical or oval, or the like.

C. Structural Factors

Another class of factors that are generally considered in the design methods of the present invention are structural characteristics of the microfluidic devices and channel networks. Such characteristics include the nature of the materials from which the channel networks are fabricated. For example, the nature of the charge present on the surface of a microfluidic channel can have profound effects on electrokinetic movement of materials through those channels, as well as other interactions between the surface and the material, e.g., adsorption.

Additionally, the nature of the material and fabrication techniques can affect the cross-sectional dimensions of the channels of the network. For example, silica-based substrates, e.g., glass, quartz, fused silica, and the like are generally fabricated into microfluidic systems using lithographic techniques, e.g., photolithography, wet-chemical etching, and the like. Because these etching processes in many of these amorphous substrates are generally anisotropic, i.e., they etch equally in all directions, it is generally very difficult to produce channels having large aspect ratios (depth to width ratios greater than 1, e.g., deeper than wide). Accordingly, channel design parameters for many of these substrate types are constrained to channels having these aspect ratios.

D. Design Examples and Calculations

1. First Exemplary High Throughput Screening Assay Device Design

In a first example, a microfluidic device is desired that will be capable of performing a screening assay, e.g., an enzyme assay in continuous flow mode, while periodically introducing a different test compound from a library of test compounds that is separate from the device, e.g., through a pipettor channel integrated with the device. Thus, as a general requirement, the device includes a main reaction channel in which the reaction is to be carried out. The main reaction channel is fluidly connected to the pipettor channel in order to introduce the test compounds into the reaction channel. The device also typically includes at least two side channels intersecting the main channel, in order to introduce the reaction components and potentially a dilution buffer into the main reaction channel.

In the present example, the assay to be performed is relatively simple, and does not require a separation step. As such, a simple pressure-based driving force is selected to drive the flow of fluids through the device.

Based upon these initial criteria, a general schematic of the channel network of the device can be laid out, e.g., as shown in FIG. 1A. As shown in FIG. 1A, the device 100 comprises a planar body structure 102, and includes the main reaction channel 104 disposed within its interior. The main channel is fluidly connected to an external pipettor element 106 at one end, and with a waste well 108 fluidly connected to the other end. Side channels 110 and 112 intersect and are in fluid communication with main channel 104, and are also fluidly connected to reagent wells 114 and 116, respectively. Also as shown, fluid flow through the device is driven through the application of a vacuum at the waste port/reservoir 108.

Again, assuming that one is performing a simple assay operation within the channel network, a sample or test compound is introduced into the main reaction channel 104 through the pipettor element 106, and mixed with two reactants within channel 104, which reactants are brought in from wells 114 and 116 via channels 110 and 112. Within channel 104, the sample and reactants are allowed to remain in contact as they flow along the main channel 104, toward waste reservoir 108. The sample and reagents are then typically transported past a detection window, 116, at which point the results of the reaction between the sample and the reagents are ascertained by an appropriate detection system.

Figure 1B:
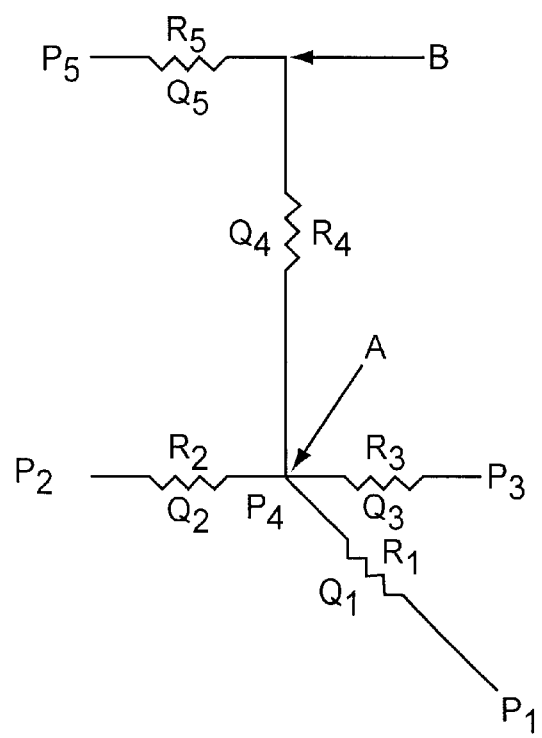
FIG. 1 schematically illustrates a microfluidic channel geometry for performing serial analysis on a number of samples contained in external reservoirs.
FIG. 1C illustrates a mask design for an actual channel network designed in accordance with the methods and parameters of the present invention and as schematically illustrated in FIGS. 1A and 1B.
FIG. 1D illustrates a plot of actual microfluidic characterization data obtained using the channel network shown in FIG. 1C.

For an exemplary channel network, and with reference to the channel network illustrated in FIGS. 1A and 1B, a particular assay may require the following reaction parameters or requirements:

(1) 15–20% flow rate from the reagent or side channels;
(2) up to 25 seconds for reaction time;
(3) a pressure drop ($\Delta P$) of at least 30,000 dyn/cm$^2$ (12" of water) between $P_1$ and $P_4$, e.g., to minimize effects of spontaneous injection at the tip of the pipettor element.

In the case of this exemplary system, the amount of time that the sample and reagents are allowed to react within the main channel 104 is dictated by the length of the channel portion between the point at which the reagents are introduced and the detection point, e.g., between points A and B, as well as the average flow velocity of the materials through that channel segment. The average flow velocity is in turn a function of the flow rate and the cross-sectional area of the channel.

The flow rate in a pressure or vacuum driven system is dictated in part by the amount of pressure or vacuum applied to the system. In pressure driven flow of fluids through channels, one generally considers the flow resistance (R) that the channel network presents to fluid flow through the channels. The total resistance of the system (R) is made up of the sum of the resistances of the individual channel segments $R_n$. In FIG. 1B, each of the channel segments is schematically illustrated and assigned its own channel resistance. For example, the level of flow resistance in the pipettor element channel 106 is designated as $R_1$. The flow resistance in side channels 114 and 116 is designated as $R_2$ and $R_3$, respectively, while the resistance through channel 104 is designated as $R_4$ and $R_5$.

For this pressure-based system, therefore, the overall pressure balance is given by the equation:

$$\Delta P = QR \quad (1)$$

where P is the applied pressure differential, Q is the flow rate, and R is the equivalent flow resistance of the entire channel system. In the case of the channel system illustrated in FIGS. 1A and 1B, the flow resistance (R) in the case that $P_1$, $P_2$, and $P_3$ are equal, e.g., atmospheric pressure, is provided as follows:

$$R = R_4 + R_5 + \left(\frac{1}{R_1} + \frac{1}{R_2} + \frac{1}{R_3}\right)^{-1} \quad (2)$$

As noted above, in the case of externally obtained samples, e.g., those obtained through an external pipettor element or capillary, the pressure $P_1$ at the end of the pipettor channel $R_1$ varies due to spontaneous injection at the pipette inlet during transfer of the pipette tip from one fluid source to another. This spontaneous injection pressure arises from the curvature of the tiny drop of fluid hanging at the tip of the pipette, and is dictated by the surface tension of the buffer and the radius of the drop. For example, for a capillary with an aqueous buffer drop having a diameter of 360 $\mu$m, spontaneous injection increases $P_1$ by 3000 to 7500 dyn/cm$^2$ (1 to 3 inches of water of pressure) above atmospheric depending on the surface tension of the buffer. The effects of this fluctuation in pressure can be minimized when the pressure point at $P_4$, where the reagents channels meet the main channel, is far away from atmospheric and therefore $P_1$.

To determine the effect on flow rate due to spontaneous injection, one can solve for the values of all internal pressure nodes and flow rates using the equivalence of Ohm's law and Kirchkoff's current law, in which pressure is analogous to voltage, flow rate to current, and hydrodynamic resistance to electrical resistance. These analogous equations are valid because the flow in the typical microfluidic channels is in the low Reynolds number regime in which inertia effects are negligible and pressure is linearly proportional to flow rate.

With reference to the circuit diagram of FIG. 1B, unknown flow rates $Q_1$, $Q_2$, $Q_3$ and $Q_4$ (flow rates in each of the different channel segments having the resistances $R_1$, $R_2$, $R_3$ and $R_4$, respectively) and unknown pressure $P_4$, can be calculated by the following equations, given pressures $P_1$, $P_2$, $P_3$ and $P_5$:

$$P_1 - P_4 = Q_1 R_1 \quad (3)$$

$$P_2 - P_4 = Q_2 R_2 \quad (4)$$

$$P_3 - P_4 = Q_3 R_3 \quad (5)$$

$$P_4 - P_5 = Q_4(R_4 + R_5) \quad (6)$$

$$Q_4 = Q_1 + Q_2 + Q_3 \quad (7)$$

Solving for P4 from Eq. 3 yields $$P_4 = P_1 - Q_1 R_1 \quad (8)$$

Then solving for the values of $Q_1$–$Q_4$, according to the following equations:

$$Q_2 = \frac{P_2 - P_4}{R_2} = \frac{P_2 - P_1 + Q_1 R_1}{R_2} \quad (9)$$

$$Q_3 = \frac{P_3 - P_4}{R_3} = \frac{P_3 - P_1 + Q_1 R_1}{R_3} \quad (10)$$

$$Q_4 = Q_1 + \frac{P_2 - P_1 + Q_1 R_1}{R_2} + \frac{P_3 - P_1 + Q_1 R_1}{R_3} \quad (11)$$

Solving now for $Q_1$ from equations (1), (2), (3) and (4), yields the following equation:

$$Q_1 = \frac{P_1 - P_5 - (P_2 - P_1)\left(\frac{R_4 + R_5}{R_2}\right) - (P_3 - P_1)\left(\frac{R_4 + R_5}{R_3}\right)}{R_1 + R_4 + R_5 + \frac{R_1}{R_2}(R_4 + R_5) + \frac{R_1}{R_3}(R_4 + R_5)} \quad (12)$$

Based upon the above calculations, the optimal dimensions for each of the channel segments which satisfy all the specifications mentioned above, including limiting the effects of spontaneous injection at the capillary element, are calculated as shown in Table 1 below.

TABLE 1

| Channel | Depth ($\mu$m) | Width ($\mu$m) | Length (mm) | Viscosity (Poise) | Resistance (g/cm$^4$s) | Flow rate (cm$^3$/s) | Dilution Factor |
|---|---|---|---|---|---|---|---|
| $R_1$ | 20 | | 20 | 0.01 | $5.1 \times 10^{10}$ | $6.4 \times 10^{-7}$ | 0.64 |
| $R_2$ | 12 | 29 | 55 | 0.01 | $1.8 \times 10^{11}$ | $1.8 \times 10^{-7}$ | 0.18 |
| $R_3$ | 12 | 29 | 55 | 0.01 | $1.8 \times 10^{11}$ | $1.8 \times 10^{-7}$ | 0.18 |
| $R_4$ | 12 | 74 | 32 | 0.01 | $3.3 \times 10^{10}$ | $1.0 \times 10^{-6}$ | |
| $R_5$ | 12 | 74 | 13 | 0.01 | $1.4 \times 10^{10}$ | $1.0 \times 10^{-6}$ | |

These calculations are done for the case when the tip of the pipette element is submerged in the fluid reservoir, and $P_1$, $P_2$ and $P_3$ are at atmospheric pressure. The dilution factors from the capillary ($R_1$) and side channels ($R_2$ and $R_3$) are calculated as the ratio of the flow rate in each of these channels to the flow rate in the main channel $R_4$. In a typical experiment, $P_5$ is at $-80,000$ dyn/cm$^2$ (31" of water below atmospheric), and the reaction time in the main channel $R_4$ is 25 seconds, which satisfies the design specification.

In the analysis of flow rate variations due to spontaneous injection, $P_1$ is assumed to change from atmospheric to 5000 dyn/cm$^2$ (2" of water pressure). The analysis results are summarized in Table 2.

TABLE 2

| | Without Spontaneous Injection | | | With Spontaneous Injection | | | % diff. |
|---|---|---|---|---|---|---|---|
| n | $P_n$ (dyn/cm$^2$) | $Q_n$ (cm$^3$/s) | Dilution factor | $P_n$ (dyn/cm$^2$) | $Q_n$ (cm$^3$/s) | Dilution factor | in flow rate |
| 1 | 0 | $6.4 \times 10^{-7}$ | 0.64 | 5,000 | $7.0 \times 10^{-7}$ | 0.67 | $-5.4$ |
| 2 | 0 | $1.8 \times 10^{-7}$ | 0.18 | 0 | $1.7 \times 10^{-7}$ | 0.17 | 9.5 |
| 3 | 0 | $1.8 \times 10^{-7}$ | 0.18 | 0 | $1.7 \times 10^{-7}$ | 0.17 | 9.5 |
| 4 | $-32,600$ | $1.0 \times 10^{-6}$ | | $-35,800$ | $1.0 \times 10^{-6}$ | | |
| 5 | $-80,000$ | $1.0 \times 10^{-6}$ | | $-80,000$ | $1.0 \times 10^{-6}$ | | |

Figure 1C:
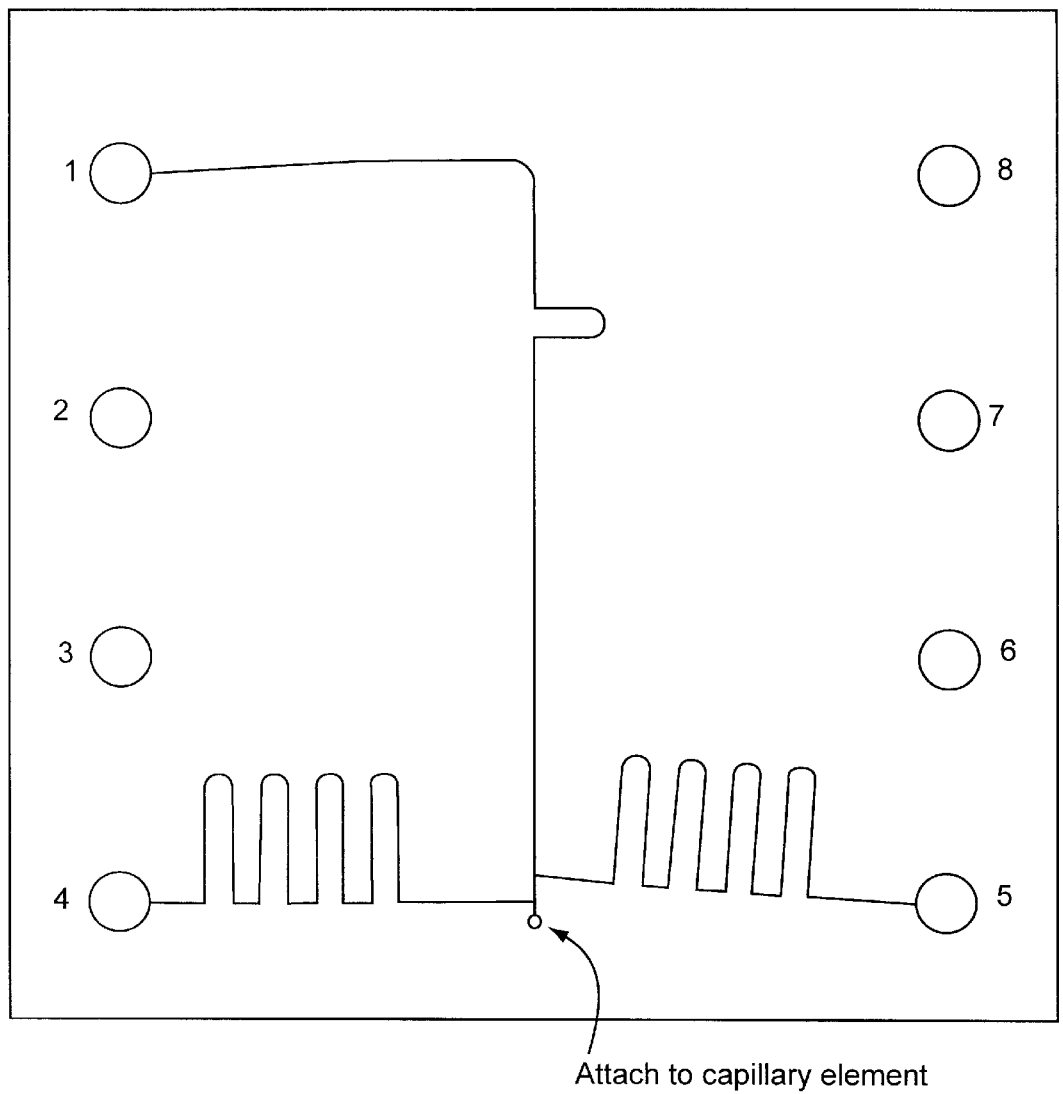
Figure 1D:
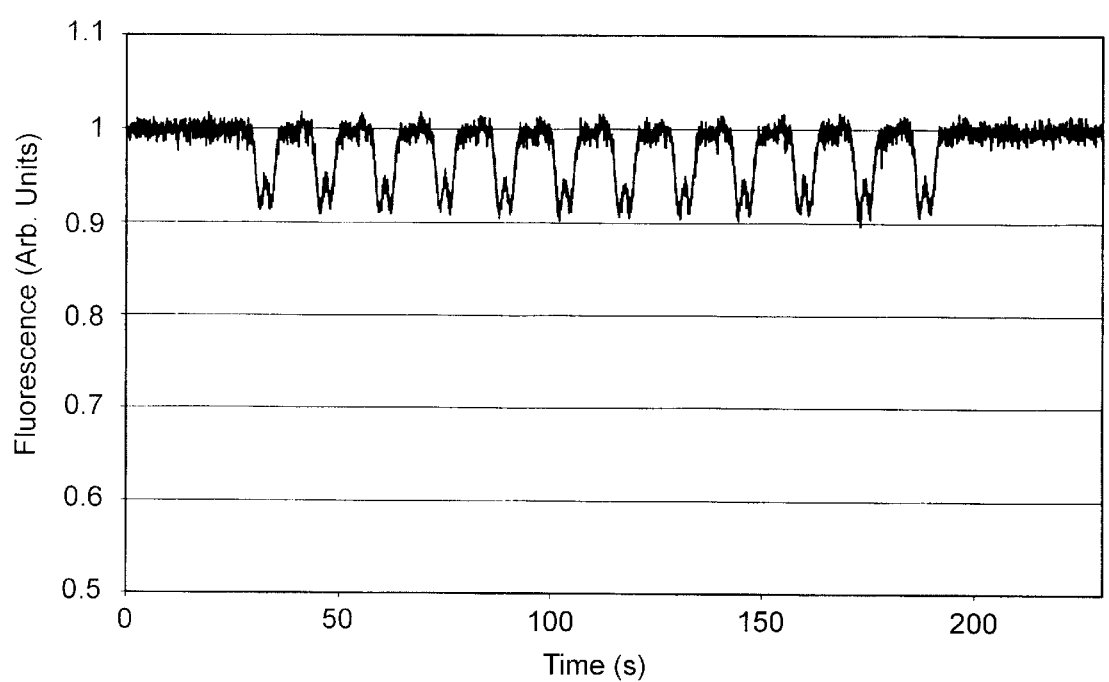

As can be seen, spontaneous injection is expected to induce about 10% variation in the flow rate from the side channels. FIG. 1C is a mask drawing of the planar part of a pipettor microfluidic device based on the channel dimensions specified in Table 1. FIG. 1D illustrates experimental results characterizing the flow of this device. In this experiment, a fluorescent dye solution was placed in the reagent wells 4 and 5, which are connected to side channels $R_2$ and $R_3$, and the capillary element was programmed to sample fluids sequentially from a series of 12 external reservoirs using a vacuum applied to waste well 1. The flow rate variations due to spontaneous injection was manifested as a decrease in the dye fluorescence intensity. The valleys in the intensity are about 10% of the total baseline signal, which is in good agreement with the expected drop in flow rate in the side channels as shown in Table 2.

2. Second Exemplary High Throughput Screening Assay Device Design

A microfluidic device was desired, which incorporated an external sampling pipettor element ("capillary") with a rectangular reaction channel ("channel"), which utilized pressure driven flow to mix enzyme and substrate within the reaction channel while periodically introducing test compounds through the capillary element, substantially as described above. Again, the device included the general layout of the device shown in FIGS. 1A and 1B, as described above. However, unlike the example provided above, it was desired to optimize throughput rates for the device in view of dispersion effects of the reagents within the channels.

Specifically, in order to optimize throughput in the overall device, it is necessary to introduce successive sample fluid plugs into the reaction channel through the capillary element, as closely spaced as possible, without excessive diffusive or dispersive intermixing of successive sample plugs, whether adjacent or separated by an appropriate spacer fluid plug.

Calculation of dispersion rates and distances within microfluidic channel networks is described in, e.g., copending U.S. application Ser. No. 09/233,700, filed Jan. 19, 1999, and incorporated herein by reference in its entirety for all purposes.

Table 3 (left column) illustrates the input values for the system, based upon the predetermined channel geometry and or assay requirements. Table 3 (right column) illustrates the optimized values for the remaining variables, once the predetermined or preordained values are ascertained.

TABLE 3

| INPUT: | | CALCULATED: | |
|---|---|---|---|
| Channel Dimensions | | In Channel | |
| Width (a) | 74 | Max. velocity (cm/s) | 0.22 |
| Depth (b) | 12 | Avg. velocity (cm/s) | 0.13 |
| Reactor length (cm) | 3.2 | Inhibitor E (cm$^2$/s) | $2.51 \times 10^{-4}$ |
| Main channel Length (cm) | 4.7 | Substrate E (cm$^2$/s) | $7.53 \times 10^{-4}$ |
| Cross-section Area (cm$^2$) | $8.88 \times 10{-6}$ | Enzyme E (cm$^2$/s) | $1.51 \times 10^{-3}$ |
| Aspect ratio (b/a) | 0.16 | In capillary | |
| Ua/Um | 0.58 | Max Velocity (cm/s) | 0.72 |
| f(b/a) | 6.7 | Avg. velocity (cm/s) | 0.36 |
| Capillary Dimensions | | Inhibitor E (cm$^2$/s) | $9.1 \times 10{-4}$ |
| Inner Diameter (μm) | 20 | Substrate E (cm$^2$/s) | $2.7 \times 10{-3}$ |
| Outer Diameter (μm) | 365 | Enzyme E (cm$^2$/s) | $5.5 \times 10{-3}$ |
| Length (cm) | 2 | Total time in cap. | 5.53 |
| Area (cm$^2$) | $3.1 \times 10^{-6}$ | Dispersion (L) | |
| Area ratio (chan./cap.) | 2.8 | Inhib. in Cap. (cm) | 0.10 |
| Buffer/Analyte Prop. | | Inhib. in Channel (cm) | 0.11 |
| Inhibitor Diff. (cm$^2$/s) | $3 \times 10^{-6}$ | Subst. in Channel (cm) | 0.19 |
| Substrate Diff. (cm$^2$/s) | $1 \times 10^{-6}$ | Enz. in Channel (cm) | 0.27 |
| Enzyme Diff. (cm$^2$/s) | $5 \times 10^{-7}$ | Limiting disp. (cm) | 0.27 |
| Buffer Visc. (cP) | 1 | Init. plug L/disp. L (cm) (n) | 6.0 |
| Incubation Time | | Spacer length in chan. (cm) | 0.82 |
| Time in Channel (s) | 25 | Sample Length in chan. (cm) | 0.82 |
| Pressure Drop (psi) | 1.6 | Spacer length in cap. (cm) | 2.33 |
| | | Sample length in cap. (cm) | 2.33 |
| | | Dwell time spacer(s) | 6.4 |
| | | Dwell time sample (s) | 6.4 |
| | | 1/throughput (s/sample) (P) | 12.9 |

As can be seen from Table 3, above, a number of assay and channel parameters were predetermined and/or preordained based upon the assay that was to be performed in the device to be performed, e.g., buffer/analyte properties and incubation time, as well as practicalities of the microfluidic device structure, e.g., channel and capillary dimensions. For example, incubation time is generally dictated by the kinetics of the assay that is to be performed. This, in turn, dictates the amount of time that a reaction mixture remains in the reaction channel, which is a function of flow rate and channel length. Similarly, channel depth can be dictated by the detection limits of the system used to detect signals within the channels, e.g., so as to permit the presence of adequate levels of signal at the detection zone.

Based upon these predetermined or preordained parameters, one can then determine other parameters that are optimized, e.g., for throughput and/or dispersion/diffusion. For example, in the example provided, values are calculated from flow velocities both in the channels of the device as well as within the external capillary element. Additionally, optimal values are provided for the length of sample fluid plugs and spacer plugs, e.g., provided between sample fluid plugs, so as to permit optimal throughput without excessive intermixing of sample plugs, e.g., minimizing spacer plug length.

3. Dose Response Assay Device

In another example, the principles of the present invention were employed in the design and fabrication of a different integrated microfluidic device. In particular, a device was desired for performing time dependent iterative reactions within a single reaction channel. The subject device was intended to introduce a first reagent into the reaction channel whereupon it would mix with a second reagent. The result of the first reaction would be detected at some point downstream of the mixing point. A third reagent, e.g., a more concentrated solution of the second reagent, would then be introduced into the reaction channel where it would mix with the first and second reagents, and the result of the reaction of these reagents would be determined. This would be repeated for two additional reagents, e.g., increasing concentrations of the second reagent. A specific intended use for such a device was to generate a dose response curve for a given reagent on a particular exemplary system, e.g., enzyme/substrate, etc., where the first reagent comprised the exemplary system components, and each successively added reagent was a successively higher concentration of an effector of that system, e.g., an inhibitor.

Figure 2A:
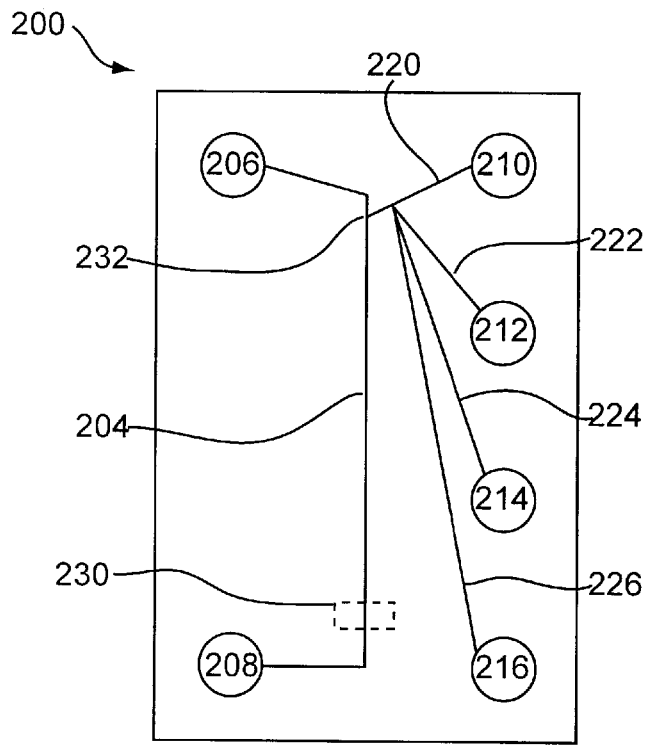
FIGS. 2A and 2B are schematic illustrations of a channel network for performing successive reactions.
Figure 2B:
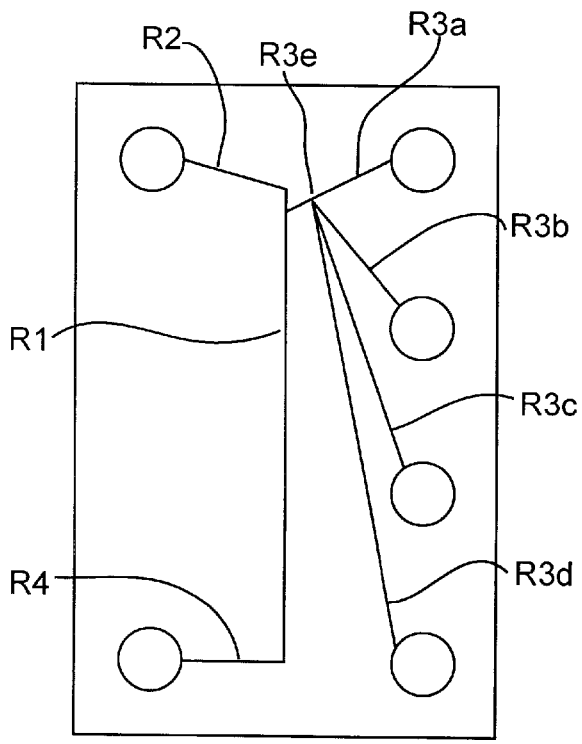

A schematic illustration of the intended device is illustrated in FIGS. 2A and 2B. As shown, the device 200 includes a main reaction channel or zone 204 which is fluidly connected to a first reagent reservoir 206 and a waste reservoir 208. Second, third, fourth and fifth reagent sources 210–216, respectively are also provided fluidly connected to the main reaction zone 204. One of the design criteria for the intended device was to be as simple as possible in terms of active fluid control. In particular, it was desired to utilize only a single driving force, e.g., a vacuum or wicking system applied to waste reservoir 208, to draw all of the reagents into and through the reaction zone 204. In order to accomplish this, it was determined that each of the channel segments (220–226) connecting reagent reservoirs 210–216 to the reaction zone 204 should be structurally configured such that reagents from each different source would reach the reaction zone at different times, thus permitting separate detection of each reagent's affect on the exemplary system. This was generally accomplished by designing the channel network such that the widths and lengths of channel segments 220–226 would deliver reagents to the reaction zone at different rates, and thus at different times, as desired. In addition, it was desired that the overall reaction time for each of the different reagents should be about 40 seconds. The segments of the various channels (e.g., channels 204 and 210–216) were each assigned resistance descriptors as shown in FIG. 2B (e.g., $R_1$–$R_4$), where the descriptor $R_{3a}$ references the portion of channel 220 between reservoir 210 and the point at which channel 220 is intersected by channels 222–226, and R3e references the segment of channel 220 between intersection 232 and the point at which channel 220 is intersected by channels 222–226. The determined dimension values for each of the channel segments is shown in Table 4, below:

TABLE 4

| Channel ID# | Depth or Diam. (μm) | Width (μm) | Length (mm) | Viscosity (Poise) | Resistance (g/(cm$^4$sec.)) |
|---|---|---|---|---|---|
| R1 | 25 | 100 | 20 | 0.1 | $1.82 \times 10^{10}$ |
| R2 | 25 | 100 | 10 | 0.1 | $9.12 \times 10^{9}$ |
| R3e | 25 | 60 | 8.4 | 0.1 | $1.46 \times 10^{10}$ |
| R3a | 25 | 60 | 8.5 | 0.1 | $1.48 \times 10^{10}$ |
| R3b | 25 | 80 | 12.3 | 0.1 | $1.47 \times 10^{10}$ |
| R3c | 25 | 100 | 16.2 | 0.1 | $1.48 \times 10^{10}$ |
| R3d | 25 | 120 | 20 | 0.1 | $1.47 \times 10^{10}$ |
| R4 | 25 | 100 | 10 | 0.1 | $9.12 \times 10^{10}$ |

For these channel dimensions, the various reaction parameters are then calculated as shown in Table 5, below. From Table 5, it can be seen that the desired goals of the intended device are met. In particular, based upon a single volumetric flow rate for each of the added reagents, e.g., in each of the connecting reagent channels, such reagents was introduced into the reaction zone at decidedly different times, so as to allow their separate detection.

TABLE 5

Applied Pressure (psi): 16.4

| Channel ID# | Flow Rate(nl/s) | Velocity (mm/s) | Time |
|---|---|---|---|
| R1 | 1.25 | 0.50 | 40.1 (rxn time in channel) |
| R2 | 0.83 | 0.33 | |
| R3e | 0.41 | 0.28 | |
| R3a | 0.10 | 0.07 | 153.4 (to introduction) |
| R3b | 0.10 | 0.05 | 266.9 (to introduction) |
| R3c | 0.10 | 0.04 | 421.6 (to introduction) |
| R3d | 0.10 | 0.03 | 608.6 (to introduction) |

A device incorporating the channel dimensions described in Table 3 was fabricated to yield the device shown in FIG. 2C, which was used to generate a dose response curve in the Examples section, below.

4. Hybrid Pressure—Electrokinetic System

In another example, it was desired to produce a microfluidic device similar to that described above, e.g., where test compounds are sipped into a reaction channel via an external sampling capillary. However, unlike the above described device, the presently described device was desired to mix the text compounds and biochemical system components, and then perform an electrokinetic mobility shift assay on the resulting mixture. Such assays are particularly useful where the assayed reaction does not itself produce a distinguishable, detectable signal, but instead results in products that have different electrophoretic mobilities.

In brief, the desired device would utilize an external sampling capillary that was connected to the main reaction channel within the body structure of the device. The two components of the biochemical system, e.g., an enzyme and a substrate would be drawn into the main reaction channel from their respective reservoirs via their respective side channels. Once present in the main channel, the flowing mixture of enzyme and substrate creates steady state level of reaction product. As noted above, however, the assayed reaction for which this device is being designed does not give rise to a detectable signal. Instead, the reaction produces product which has the same signaling capability as the substrate or precursors, but which has a different electrophoretic mobility that the substrate. Examples of such reactions include, e.g., kinase reactions, which phosphorylate compounds. The phosphorylated compounds then possess a substantially altered charge:mass ratio as a result of the addition of a highly charged phosphate group.

Accordingly, in order to differentiate substrate and product, it is desirable to subject the reaction mixture to an electric field to separate the mixture into its constituent elements. Thus, the designed device includes a separation portion to the main channel across which an electric field can be established.

Figure 3A:
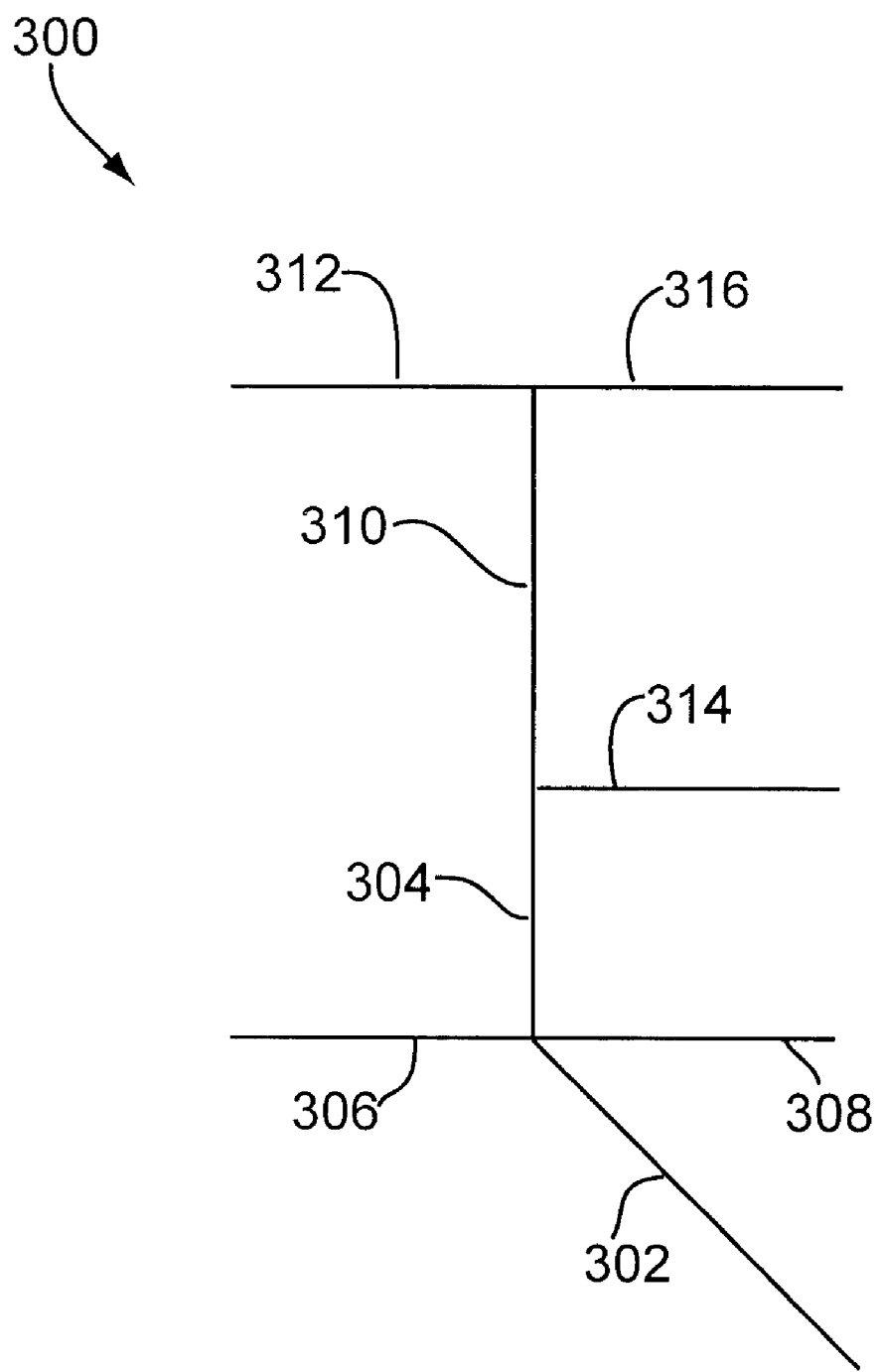
FIG. 3A schematically illustrates a microfluidic channel network configuration for use as a hybrid pressure/electrokinetic channel network.

A schematic representation of a channel network circuit diagram, which carries out such assays, is shown in FIG. 3A. As shown, the channel network 300 includes a pipettor channel segment 302 in communication with the reaction channel segment 304. Side channels 306 and 308 also intersect and fluidly communicate with the reaction channel 304. A separation channel segment 310 is provided fluidly linked or as an extension from the end of the reaction channel segment 304, opposite to the end at which channel segment 304 is in communication with the pipettor channel 302. The separation channel segment 310 is, in turn, in communication at its opposite end with waste channel 312. Side channels 314 and 316 are provided in communication with the ends of the separation channel 310 in order to provide an electric field across that channel segment. Specifically, a voltage gradient is applied between the reservoirs at the ends of these channels and through channel segment 310. Channels 314 and 316 are also referred to herein as voltage channels.

The channel network schematically shown above was intended to be used in performing a continuous flow kinase assay. Accordingly, a number of reaction parameters or requirements were determined in order to carry out the assay. The preset parameters were set as follows:

(1) 12% flow rate from each of the enzyme and reagent channels;

(2) at least 20 second reaction time for the assay (retention time in channel segment 404);

(3) at least 25 second separation time, post reaction (retention time in channel segment 410);

(4) minimize effects of spontaneous injection at capillary tip;

(5) low electrical resistance but high hydrodynamic resistance from non reagent channels, e.g., the voltage channels;

(6) channel network footprint that fits into standard eight reservoir format (e.g., as shown in FIG. 5);

(7) only double depth channel network;

(8) fluorescent detection.

From a number of these parameters, e.g., (5)–(8), it was possible to predetermine a number of channel network dimensions. For example, it was desirable to provide high hydrodynamic resistance in channels, which were not being used to add reagents, so that there would be very little fluid flow from these channels. However, as these channels were to be used to provide an electric field, it was also desired to avoid significantly increasing the electrical resistance of these channels. This is most easily accomplished by reducing a channel's depth, which reduces pressure based, or hydrodynamic flow by the third power of the depth change, whereas increase in resistance is linear with the depth change. Further, in order to accommodate a surface coating that was to be provided in order to minimize or eliminate electroosmotic flow as a result of the electric field, it was desired to keep the channel at a minimum of 3 $\mu$m deep. Accordingly, side channels 306, 308, 314, and 316 were all set at a depth of 3 $\mu$m. The remaining channels were set at 12 $\mu$m deep, in order to permit adequate detection of fluorescent species in reaction channel 304 and separation channel 310, and to permit only a double etching process, to produce a double depth channel network, rather than requiring more etching steps.

Figure 3B:
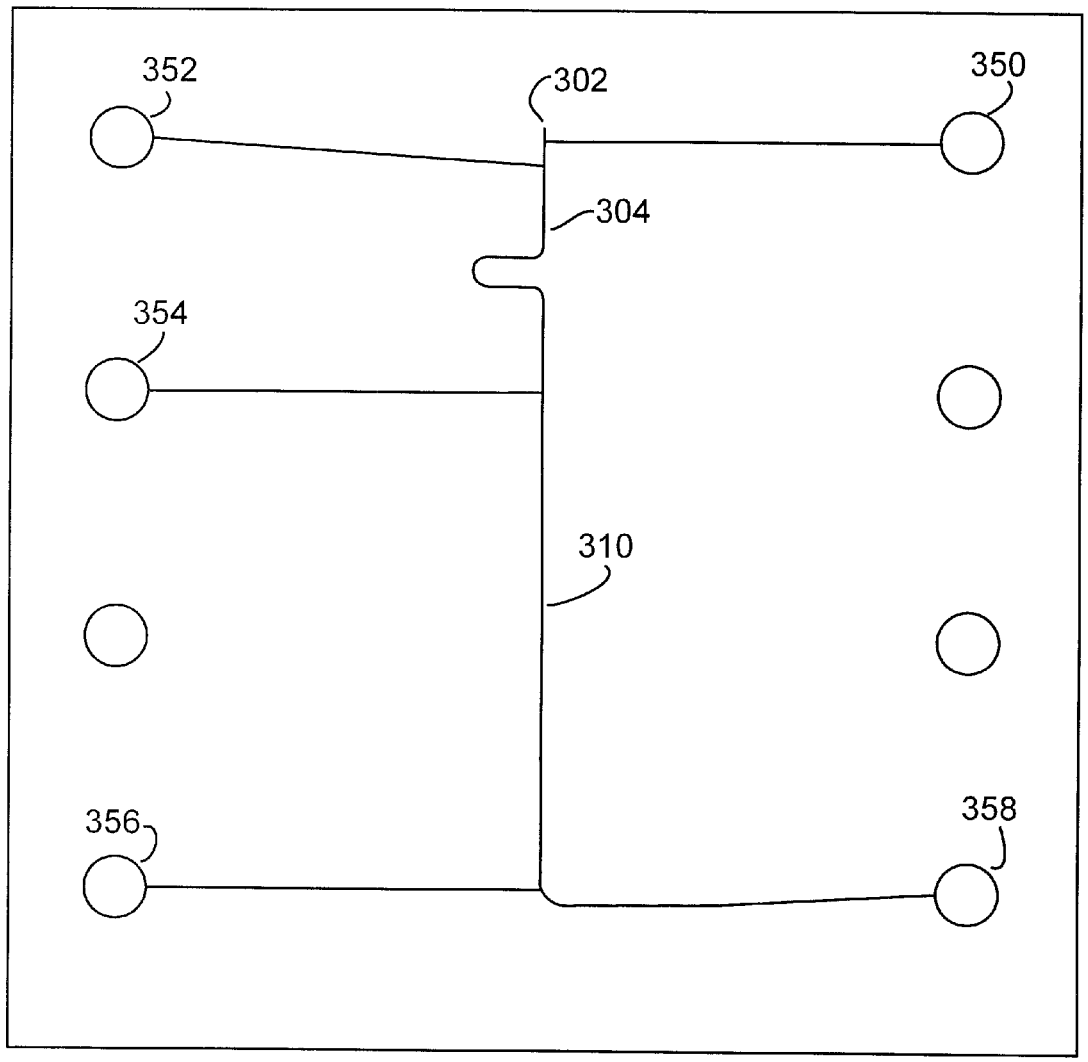
FIG. 3B illustrates a mask design for an optimized channel network in accordance with the schematically illustrated configuration of FIG. 3A.

As noted above, it was also desired to maintain the channel network within a standard reservoir footprint, e.g., as shown in FIG. 3B. Thus, in providing the channel network to accommodate this footprint, the lengths of the various channel segments were set, as provided in Table 6, below. Using all of these set parameters, the channel network was further designed in order to achieve all of the reaction parameters set forth above, e.g., (1)–(4). The calculated values for these various parameters are provided in Table 6, below, based upon a fluid viscosity of 1 centipoise. Generally, these values were calculated using substantially the same lumped circuit analysis as described above.

TABLE 6

| Channel | Depth or Diam. (μm) | Width (μm) | Length (mm) | Resistance (g/(cm⁴s)) |
|---|---|---|---|---|
| 302 | 20 (diam.) | — | 20 | $5.1 \times 10^{10}$ |
| 306 | 3 | 156 | 13 | $3.7 \times 10^{11}$ |
| 308 | 3 | 156 | 13 | $3.7 \times 10^{11}$ |
| 304 | 12 | 74 | 14 | $1.5 \times 10^{10}$ |
| 314 | 3 | 86 | 13 | $6.8 \times 10^{11}$ |
| 310 | 12 | 74 | 18 | $1.9 \times 10^{10}$ |
| 316 | 3 | 156 | 13 | $3.7 \times 10^{11}$ |
| 312 | 12 | 74 | 13 | $1.4 \times 10^{10}$ |

For these channel dimensions, the various reaction parameters, e.g., (1)–(4), are then calculated as shown in Table 7, below:

TABLE 7

Applied Pressure (in H2O) at waste reservoir: −20

| Channel ID# | Flow Rate (ml/s) | Velocity (mm/s) | Time (s) |
|---|---|---|---|
| 302 | $4.3 \times 10^{-7}$ | 1.37 | 14.6 |
| 306 | $6.0 \times 10^{-8}$ | 0.13 | |
| 308 | $6.0 \times 10^{-8}$ | 0.13 | |
| 304 | $5.5 \times 10^{-7}$ | 0.62 | 22.6 |
| 314 | $4.4 \times 10^{-8}$ | 0.17 | |
| 310 | $6.0 \times 10^{-7}$ | 0.67 | 26.9 |
| 316 | $1.1 \times 10^{-7}$ | 0.24 | |
| 312 | $7.1 \times 10^{-7}$ | 0.80 | |

Figure 3C:
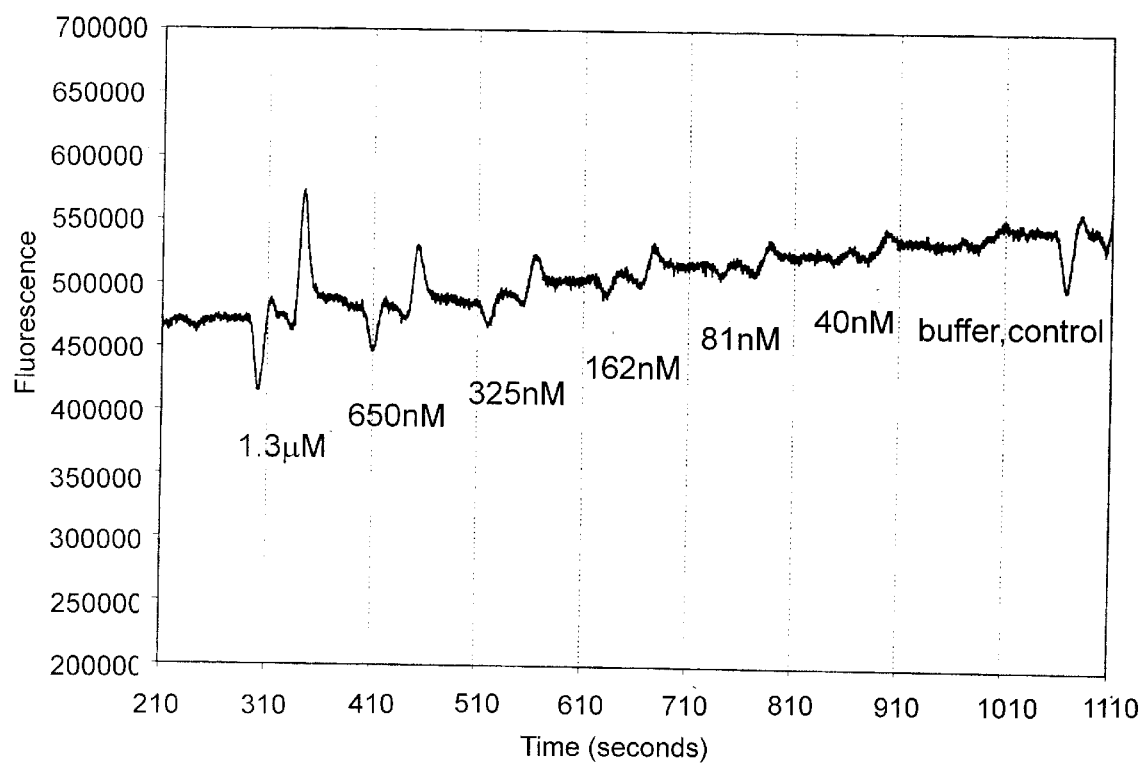
FIG. 3C is a plot of kinase inhibition data obtained using the channel network shown in FIG. 3B.

In comparing the calculated parameters shown in Table 7 to those set forth above, it can be seen that the desired goals of the device are met. In particular, the device provides for the appropriate mixture of enzyme, substrate and test compound within the reaction channel portion 304. The mixture is allowed to incubate for an appropriate length of time in channel segment 304 (e.g., 22.6 seconds), before it is subjected to separation. Following an appropriately timed incubation, the reaction products are then separated in the separation portion of the channel, e.g., channel segment 410, for an appropriate time (26.9 seconds). The device shown in FIG. 3B was used to in screening for inhibitors of enzyme activity in a non-fluorogenic assay format, and particularly, a kinase assay. The data from this analysis is shown in FIG. 3C, and the experimental details are provided in the Examples section, below.

5. Continuous Dilution System

Figure 4A:
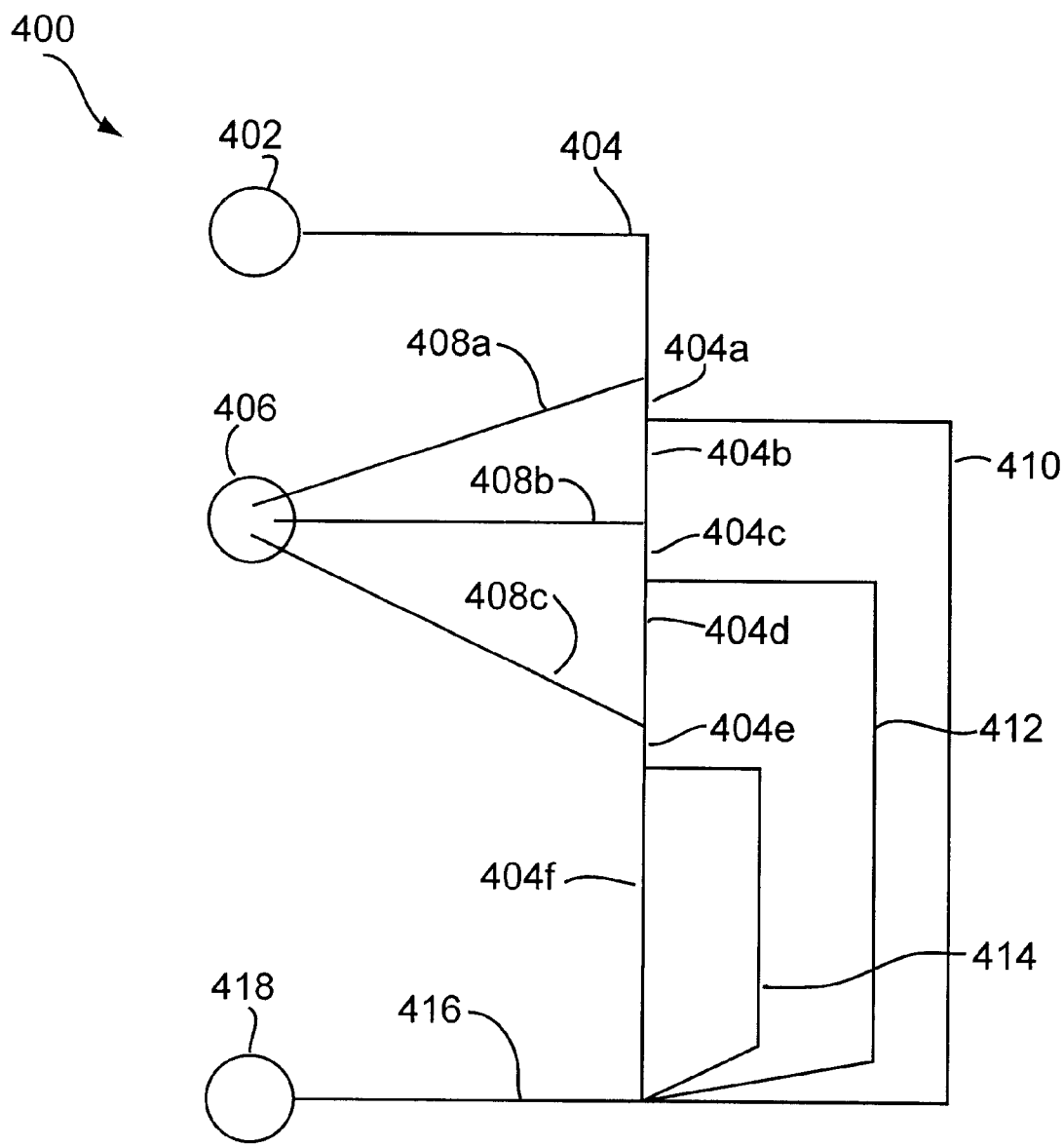
FIG. 4A is a schematic illustration of a channel configuration for performing a continuous dilution process under a single applied driving force.

In still another example, a device was desired which was capable of performing serial dilutions of materials within the channel network, but under only a single applied pressure differential, e.g., drawing at one vacuum port. A schematic illustration of a dilution module, based upon the desired goals set forth above, is illustrated in FIG. 4A. This device utilizes the general principle for a microfluidic dilution module, as described in commonly owned U.S. Pat. No. 5,869,004, which is incorporated herein by reference.

As shown, the channel network or dilution module 400 includes a sample source or reservoir 402 that is connected to a main channel 404 (incl. segments 404a–f). A diluent source 406 is also provided. The diluent source is fluidly connected to the main channel via a plurality of diluent channels, e.g., 408a–c, which intersect the main channel 404a–f, at different points. In the case of the device shown, three diluent channels are provided to provide a three-stage dilution. After the intersection with each diluent channel, a tapping channel is provided to tap of a certain volume of the diluted material resulting from each dilution stage, and making room for the subsequent dilution stage. For example, tapping channel 410 intersects the main channel at a point after diluent channel 408a (e.g., between channel segments 404a and 404b). Similarly, tapping channel 412 intersects the main channel 404, after diluent channel 408b (between channel segments 404c and 404d), while tapping channel 412 intersects the main channel 404 at a point after diluent channel 408c (between channel segments 404e and 404f).

In operation, it was desired that by applying a set vacuum to waste reservoir 418, one could draw sample material into the main channel 404 (incl. a–f). A predetermined volume or ratio of material would be brought into the main channel to mix with the sample material within channel segment 404a. In order to make room for a subsequent dilution, a predetermined amount of material would be tapped off from the main channel by tapping channel 410. A second predetermined ratio of diluent is then added to the main channel from diluent channel 408b. It should be noted that all of these samples, diluent and tapped off mixtures are continuously flowing from the time the vacuum is applied to the waste reservoir, and are being drawn by that vacuum. This dilution is repeated a desired number of times. As shown, a three-stage dilution is contemplated.

In setting out to design an optimized microfluidic device, the following parameters were identified:

(1) at least 5 seconds mixing time at each stage;

(2) overall dilution of 1:100, in three stages, thus 1:4.65 dilution ratio at each stage;

(3) simplest fabrication process, e.g., single depth etch;

(4) fluorescent detection of dilution;

(5) footprint of standard eight reservoir device.

Based upon the above parameters, it was possible to determine a number of the channel dimensions, allowing manipulation of other channel dimensions to affect the desired flow properties. For example, in order to simplify fabrication of the channel network, a single depth channel was chosen. Further, because fluorescent detection was again to be used, the channel depth was again set at 12 μm. the desired dilution factor is equivalent to the ratio of fluid moving into the main channel from a diluent channel to the fluid already flowing through the main channel. As such, the widths and lengths of the various channels were calculated to provide appropriate resistances to yield these proportional flow rates. Using all of these set parameters, the channel network was further designed in order to achieve all of the reaction parameters set forth above. The calculated values for these various parameters are provided in Table 8, below, using a fluid viscosity of 1 centipoise. Generally, these values were calculated using substantially the same lumped circuit analysis as described above.

TABLE 8

| Channel | Depth or Diam. (μm) | Width (μm) | Length (mm) | Resistance (g/(cm⁴s)) |
|---|---|---|---|---|
| 404 | 12 | 29 | 8 | $2.6 \times 10^{10}$ |
| 408a | " | 100 | 9.63 | $7.2 \times 10^{9}$ |
| 404a | " | 74 | 5 | $5.2 \times 10^{9}$ |
| 410 | " | 74 | 22 | $2.3 \times 10^{10}$ |
| 404b | " | 44 | 5 | $9.5 \times 10^{9}$ |
| 408b | " | 44 | 9.1 | $1.7 \times 10^{10}$ |
| 404c | " | 74 | 6 | $6.3 \times 10^{9}$ |
| 412 | " | 74 | 13 | $1.4 \times 10^{10}$ |
| 404d | " | 44 | 5 | $9.5 \times 10^{9}$ |
| 408c | " | 34 | 12 | $3.2 \times 10^{10}$ |
| 404e | " | 74 | 5 | $5.2 \times 10^{9}$ |

TABLE 8-continued

| Channel | Depth or Diam. ($\mu$m) | Width ($\mu$m) | Length (mm) | Resistance (g/(cm$^4$s)) |
|---|---|---|---|---|
| 414 | " | 124 | 10 | $6.0 \times 10^9$ |
| 404f | " | 34 | 18 | $4.7 \times 10^{10}$ |
| 416 | " | 124 | 9.8 | $5.8 \times 10^9$ |

For these channel dimensions, the various reaction parameters, e.g., (1)–(4), are then calculated as shown in Table 9, below:

TABLE 9

Applied Pressure (in H2O) at waste reservoir: −9

| Channel ID# | Flow Rate (ml/s) | Velocity (mm/s) | Time (s) | Dilution Factor* |
|---|---|---|---|---|
| 404 | $4.3 \times 10^{-7}$ | 0.33 | | |
| 408a | $6.0 \times 10^{-8}$ | 0.34 | | |
| 404a | $6.0 \times 10^{-8}$ | 0.60 | 8.4 | 4.58 |
| 410 | $5.5 \times 10^{-7}$ | 0.47 | | |
| 404b | $4.4 \times 10^{-8}$ | 0.21 | | |
| 408b | $6.0 \times 10^{-7}$ | 0.74 | | |
| 404c | $1.1 \times 10^{-7}$ | 0.56 | 10.6 | 4.61 |
| 412 | $6.0 \times 10^{-8}$ | 0.46 | | |
| 404d | $5.5 \times 10^{-7}$ | 0.18 | | |
| 408c | $4.4 \times 10^{-8}$ | 0.84 | | |
| 404e | $6.0 \times 10^{-7}$ | 0.49 | 10.1 | 4.63 |
| 414 | $1.1 \times 10^{-7}$ | 0.26 | | |
| 404f | $6.0 \times 10^{-8}$ | 0.12 | | |
| 416 | $5.5 \times 10^{-7}$ | 0.85 | | |

*At the dilution stage that was completed within particular channel segment.

As can be seen from Table 9, the channel segments are provided having more than sufficient length to adequately mix sample and diluent. Further, the calculated dilution factor for each stage closely tracks the desired dilution factor of 4.65.

Figure 4B:
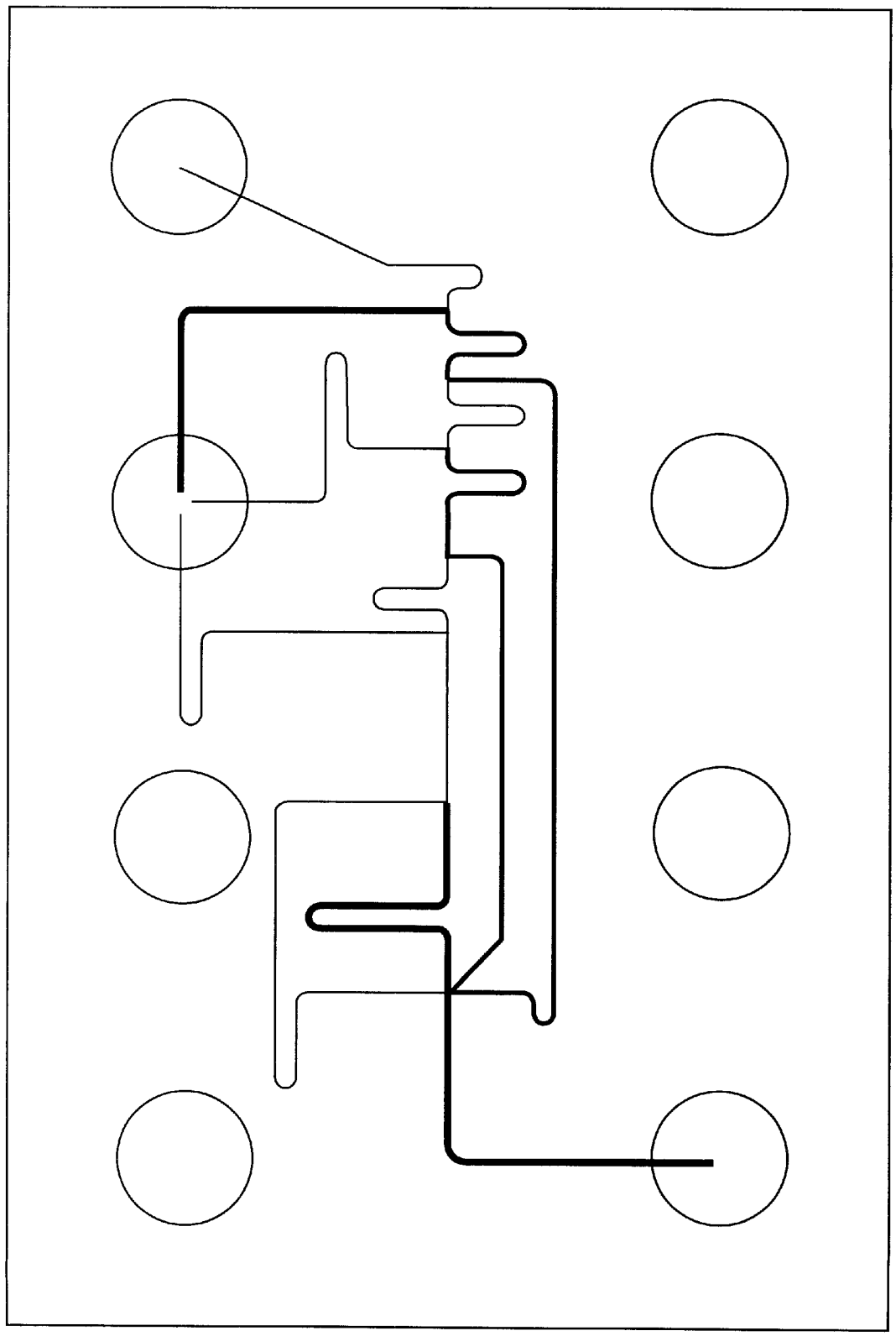
FIG. 4B is a mask design for an optimized channel network in accordance with the configuration shown in FIG. 4A.
Figure 4C:
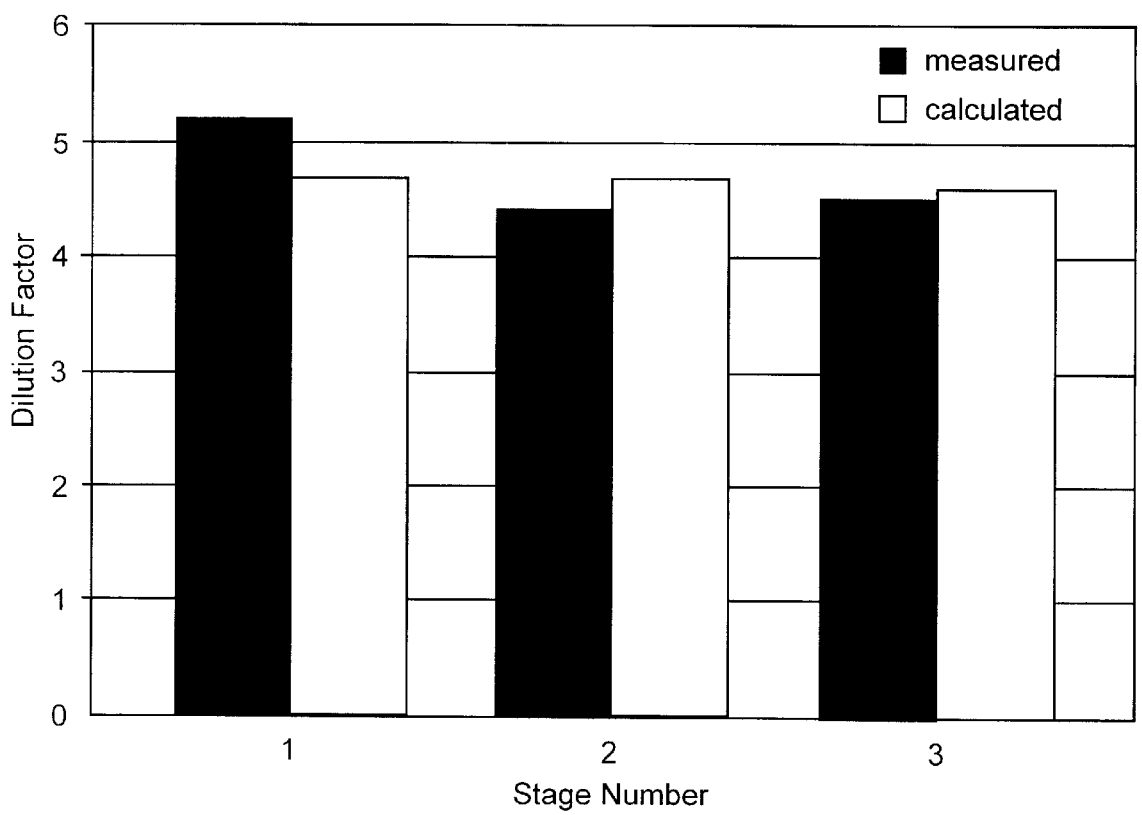
FIGS. 4C and 4D are plots of actual dilutions carried out using the channel configuration shown in FIG. 4B vs. calculated dilution factors per stage (FIG. 4C) and overall (FIG. 4D).
Figure 4D:
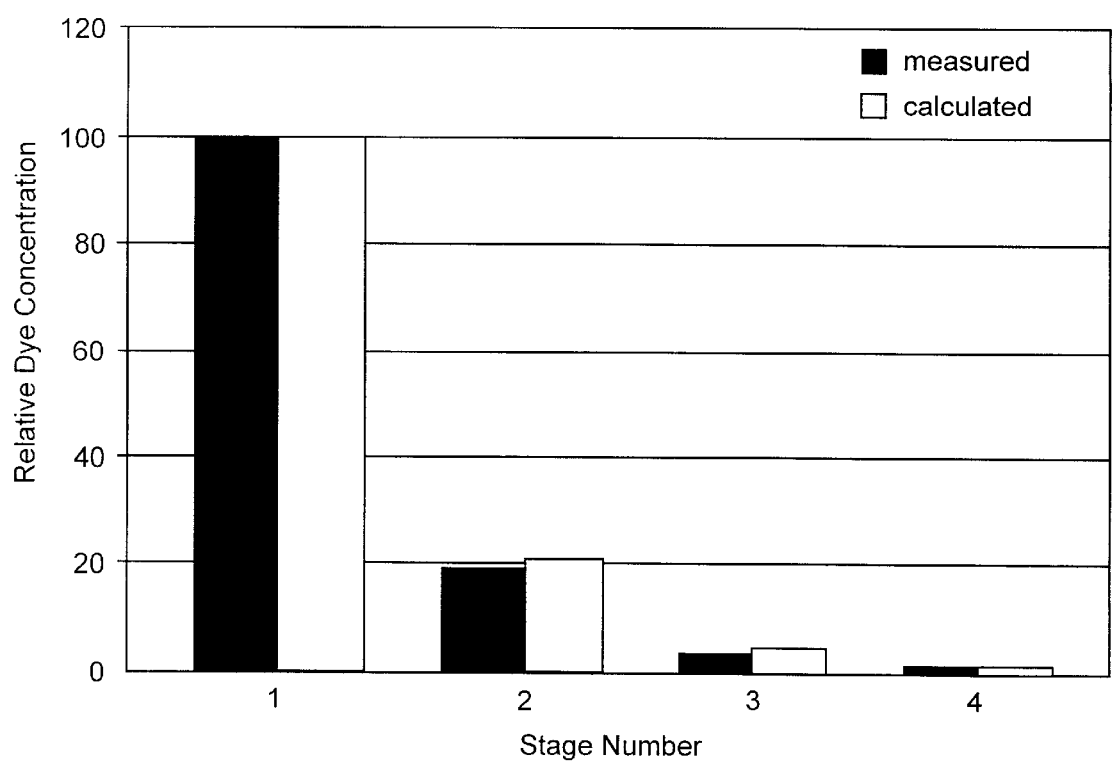

FIG. 4B illustrates the channel network actually designed in accordance with these parameters. Reference numbers from FIG. 4A are used to indicate the same components of the device shown in FIG. 4B. Dilution data generated from the device of FIG. 4B is illustrated in FIGS. 4C and 4D and compared to the expected dilution. This experiment is described in greater detail, below in the Examples section.

V. Computer Software for Implementing Design Methods

In addition to the above-described methods for designing microfluidic devices, the present invention also provides computer software that embodies these methods. Specifically, the software of the present invention generally calculates optimal channel dimensions, e.g., length, width and/or depth, based upon user input criteria, namely the selected driving force and one or more reaction criteria/parameters.

Briefly, the computer software typically receives input from the user regarding the nature of the driving force that is to be used in operating the device, at least one reaction requirement for the particular analytical reaction to be performed, which requirement is desired to be optimized. The software then calculates and provides to the user in a convenient format, the dimensions of at least first, second and third channel segments in the channel network, which dimensions include first, second and third lengths for the first, second and third channel segments, respectively, and at least a first cross-sectional dimension for each of the first, second and third channel segments. The provided dimensions thus provided are substantially optimized for the at least one reaction requirement. Alternatively, or additionally, the software performs additional steps in the fabrication of the ultimate channel network, e.g., generating a mask design for photolithographically patterning the channel network into an appropriate solid substrate, e.g., glass, quartz, silicon, or the like.

Figure 5A:
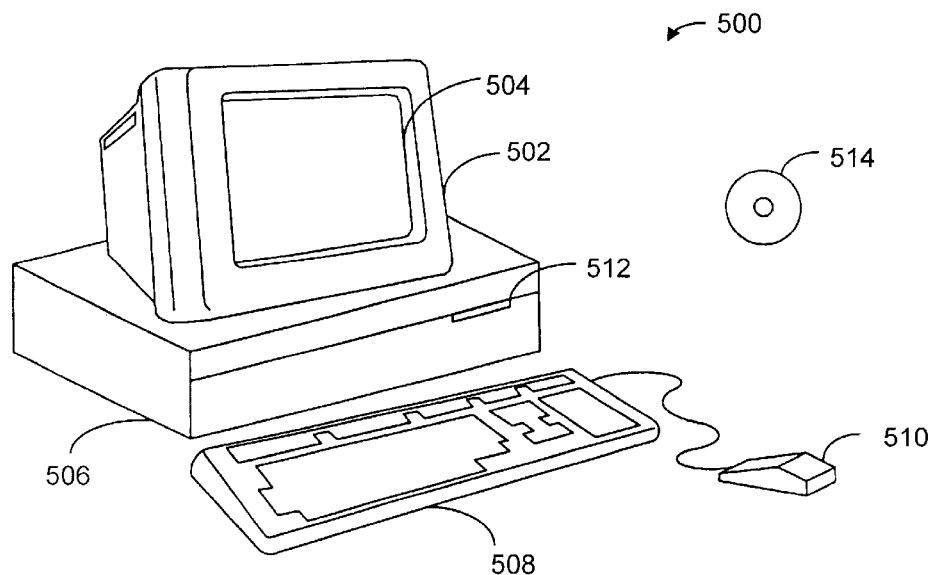
FIGS. 5A and 5B illustrate an exemplary computer system and architecture, respectively, for carrying out software embodiments of the methods of the present invention.
Figure 5B:
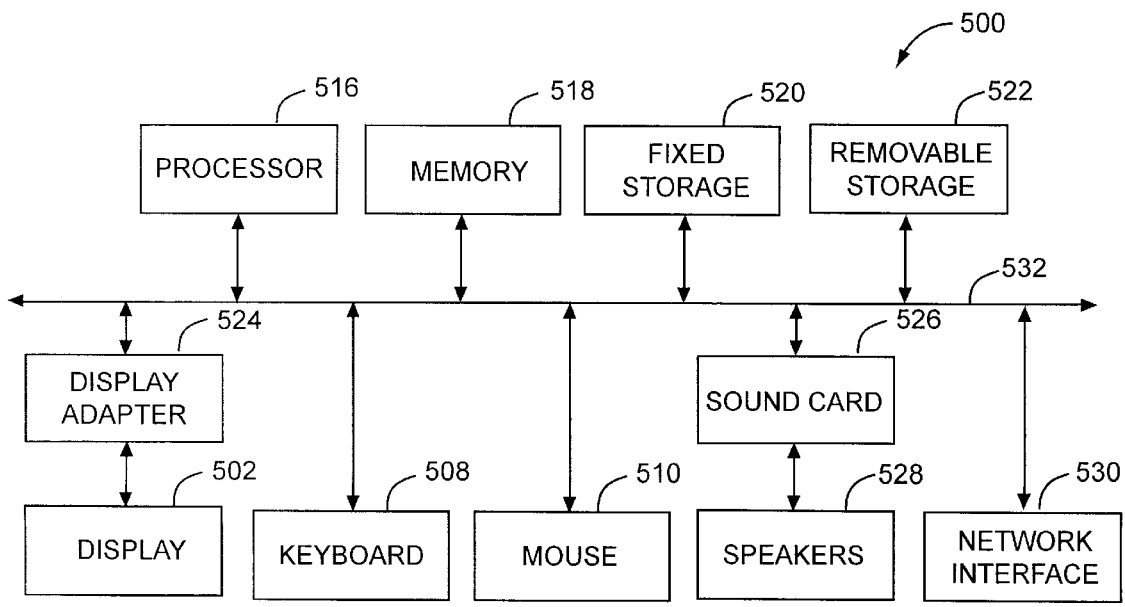

An example of a computer system that may be used to execute software for use in practicing the methods of the invention or in conjunction with the devices and/or systems of the invention is shown in FIGS. 5A and 5B. Computer system 500 typically includes a display 502, screen 504, cabinet 506, keyboard 508, and mouse 510. Mouse 510 may have one or more buttons for interacting with a graphical user interface (GUI). Cabinet 506 typically houses a CD-ROM drive 512, system memory and a hard drive (see FIG. 5B) which may be utilized to store and retrieve software programs incorporating computer code that implements the methods of the invention and/or controls the operation of the devices and systems of the invention, data for use with the invention, and the like. Although CD-ROM 514 is shown as an exemplary computer readable storage medium, other computer readable storage media, including floppy disk, tape, flash memory, system memory, and hard drive(s) may be used. Additionally, a data signal embodied in a carrier wave (e.g., in a network, e.g., internet, intranet, and the like) may be the computer readable storage medium.

FIG. 5B schematically illustrates a block diagram of the computer system 500, described above. As in FIG. 5A, computer system 500 includes monitor or display 502, keyboard 508, and mouse 510. Computer system 500 also typically includes subsystems such as a central processor 516, system memory 518, fixed storage 520 (e.g., hard drive) removable storage 522 (e.g., CD-ROM drive) display adapter 524, sound card 526, speakers 528 and network interface 530. Other computer systems available for use with the invention may include fewer or additional subsystems. For example, another computer system optionally includes more than one processor 514.

The system bus architecture of computer system 500 is illustrated by arrows 532. However, these arrows are illustrative of any interconnection scheme serving to link the subsystems. For example, a local bus could be utilized to connect the central processor to the system memory and display adapter. Computer system 500 shown in FIG. 5A is but an example of a computer system suitable for use with the invention. Other computer architectures having different configurations of subsystems may also be utilized.

The invention is further illustrated with reference to the following non-limiting examples.

EXAMPLES

Example 1

Optimized Dose Response Device

Figure 2C:
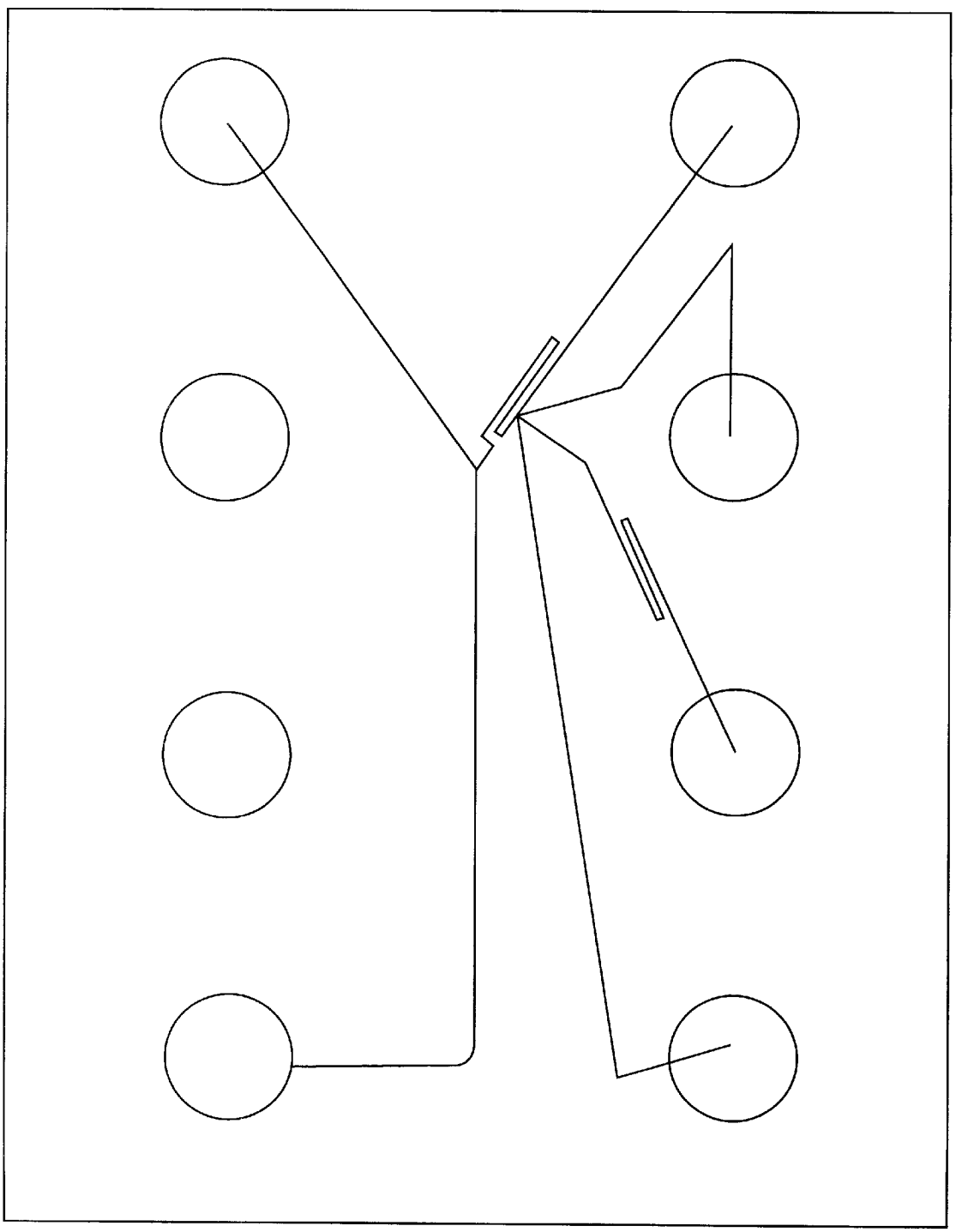
FIG. 2C illustrates the actual channel layout of a microfluidic device designed according to the specifications set for the channel network shown in FIG. 2A and optimized for the analysis to be performed.

The device shown in FIG. 2C was fabricated and used to test the dose response of a human monocytic leukemia cell line that carried the Gq coupled P2u purinergic receptor (THP-1), as a model calcium flux assay. Briefly, a phospholipase C/IP3/calcium signal transduction pathway is activated when the receptor binds to its ligand, UTP. When the cells are preloaded with a calcium sensitive indicator, i.e., Fluo-3 or Fluo-4 (available from Molecular Probes, Eugene, Oreg.), the transient increase in intracellular calcium is then detected as a fluorescent signal.

In the present example and with reference to FIGS. 2A and 2C, THP-1 cells were preloaded with Fluo-3 or Fluo-4, as well as a nucleic acid stain (Syto-62 from Molecular Probes). The cells were washed and resuspended in Cell Buffer (1.56 ml HBSS, 0.94 ml 33% Ficoll, 5 μl HEPES (1 M stock), 25 μl 100×PBC, 25 μl 10% BSA, and 0.546 ml OPTI-Prep (65% stock)) and added to reservoir 206. Different concentrations of UTP in Cell Buffer (100, 300, 1000 and 3000 nM, respectively) were then added to reagent reservoirs 210–216. Flow of cells and reagents was initiated by placing a wicking material into the waste well, specifically, two wetted glass fiber filter discs, cut to the dimensions of the waste well and stacked into well 208. A fluorescent detector employing a blue LED as an excitation source was focused at a point 230 in the reaction channel 204, 3 mm from the intersection 232 of the reaction channel 204 and the various connecting channels 220–216 ("the cell-drug intersection"). The system had a flow rate of 0.2 mm sec., which resulted in detection of cellular response 15 seconds after initial exposure to the UTP solutions. The configuration of the connecting channels 210–216 sequentially exposed the cells to increasing concentrations of UTP, e.g., 100 nM, 300 nM, 1000 nM and 3000 nM.

Figure 2D:
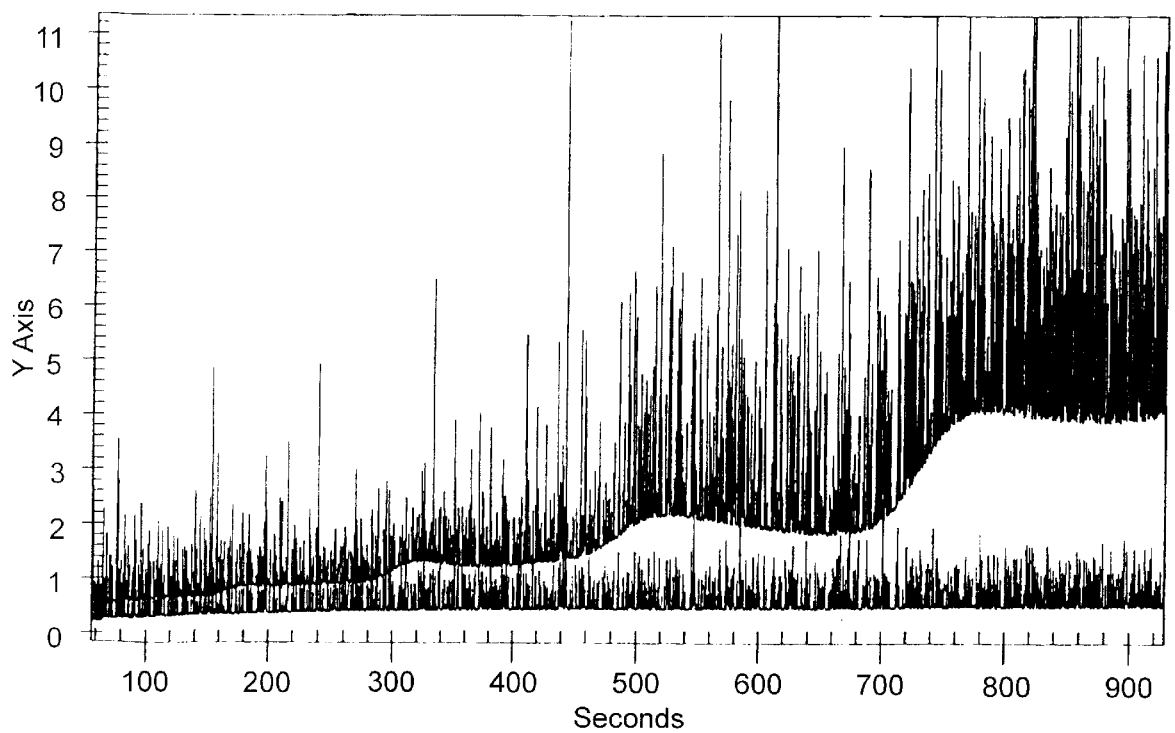
FIG. 2D illustrates raw data obtained in the determination of a dose response in the microfluidic channel network shown in FIG. 2B.
Figure 2E:
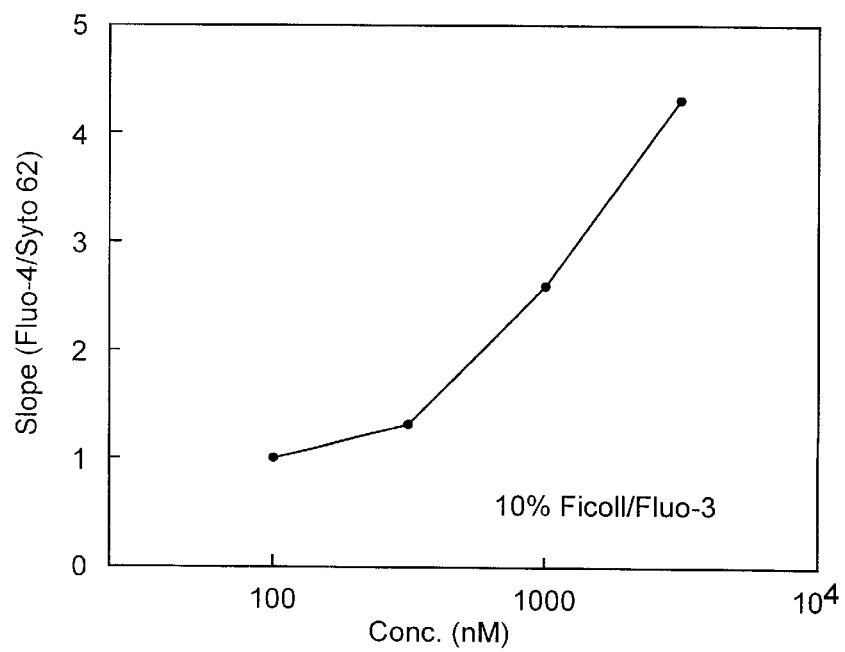
FIG. 2E illustrates a dose response curve generated from the raw data shown in FIG. 2D.

In order to monitor the stepwise increase of each UTP reagent solution, an additional marker solution, BODIPY-arginine, was added to the reagent reservoirs 210–216. The raw data from the assay are shown in FIG. 2D. As can be seen, the baseline for the detected response (upper data set) increases in a stepwise fashion, as a result of the added BODIPY-arginine dye. In addition, the signals from each cell, the peaks increase discernibly in size with each stepwise addition of the UTP reagent. FIG. 2E illustrates a dose response curve calculated from the data shown in FIG. 2D. Briefly, the slope of calcium signal (response) vs. Syto 62 signal (cell number) was calculated for each UTP concentration. That slope was then plotted against the log[UTP] to obtain the dose response curve shown in FIG. 2E. As can be seen from FIGS. 2D and 2E, the channel design methods of the present invention are effective for producing highly effective channel geometries for performing desired analyses.

Example 2

Optimized Non-Fluorogenic Assay Device

The device illustrated in FIG. 3B was used as described to perform a nonfluorogenic assay of kinase activity, and particularly, to screen for inhibition of kinase activity by inhibitors brought into the device via the external sampling capillary. In particular, Protein Kinase A (PKA) enzyme (100 nM) was placed into well 350, while the fluorescent substrate (10 μM F1-Kemptide) was placed into well 352, different concentrations of an exemplary PKA inhibitor (H-89) were sipped into the reaction channel portion 304 via an external capillary element (the entry point of which is shown as 302) at regular intervals. Flow of materials, including sipping of inhibitor was caused by applying vacuum (as described above) at waste reservoir 358. An electric field was constantly applied across the length of channel segment 310 by virtue of different voltages being applied at reservoirs 354 and 356. The process utilized a 5 second sipping time, with an overall 100 second duty cycle, e.g., reaction time plus separation time plus clearing time.

FIG. 3C illustrates a plot of the inhibition data where greatest deviation from steady state (A) is seen with highest inhibitor concentration, and incrementally smaller deviations with incrementally smaller concentrations of inhibitor (B, C, D, E and F).

Example 3

Continuous Dilution Module Design

The device illustrated in FIG. 4B was designed to carry out a 1:100 dilution of sample material in a three-stage serial dilution process. FIG. 4C is a plotted comparison of the calculated and actual dilution factor for a fluorescent dye diluted according to the above-described method and using the device shown in FIG. 4B. Briefly, fluorescent dye was placed into well 402 while diluent, e.g., buffer, was placed into well 406. A continuous vacuum of −9 inches $H_2O$ was applied to waste well 418, and detection of the relative dilutions was performed at the different dilution stages, e.g., in channel segment 404a, 404c and 404e. FIG. 4D illustrates a plot of dilution from each stage, illustrating a desired 1:100 dilution, which was closely tracked by the actual experimental dilution data.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of making a microfluidic device incorporating at least one external capillary element for performing a given analysis comprising:

providing a microfluidic device including at least one capillary element having a first end and a second end, wherein said first end of said capillary element intersects a channel network of said microfluidic device at a first intersection, said channel network comprising at least first, second and third channel segments;

providing a material transport system comprising one or more of a pressure, vacuum or electrokinetic driving force for moving fluidic materials through the channel network of the microfluidic device; and choosing a length, cross-section, or combination thereof of the first, second and third channel segments and the driving force to satisfy at least two analysis requirements for the given analysis, the first analysis requirement including minimizing an effect of spontaneous injection at the first intersection, and the second analysis requirement being selected from one or more of reaction time, separation time, reagent concentration, reagent volume, separation resolution, mixing ratio, and reaction temperature.

2. The method of claim 1 wherein the material transport system is selected to be pressure-based driving force which comprises a vacuum applied at at least one point in the channel network.

3. The method of claim 2 wherein the at least one point of the channel network comprises a port disposed in a body structure which houses the channel network, the port being in fluid communication with at least one of the first, second and third channel segments.

4. The method of claim 1 wherein the material transport system is selected to be a pressure-based driving force which comprises a positive pressure applied to at least one point in the channel network.

5. The method of claim 4 wherein the at least one point of the channel network comprises a port disposed in a body structure which houses the channel network, the port being in fluid communication with at least one of the first, second and third channel segments.

6. The method of claim 1 wherein said choosing a length, cross-section, or combination thereof for the first, second and third channel segments if performed by first computing a flow rate in each of said channel segments and said capillary element based at least in part on a calculation of an optimal value of flow resistance in each of said channel segments and said capillary element.

7. The method of claim 6 further comprising choosing the microfluidic device to include at least a fourth channel segment, wherein the flow rate in each channel segment is calculated by first calculating the flow rate $Q_1$ through the capillary element based on the following equation:

$$Q_1 = \frac{P_1 - P_5 - (P_2 - P_1)\left(\frac{R_4 + R_5}{R_2}\right) - (P_3 - P_1)\left(\frac{R_4 + R_5}{R_3}\right)}{R_1 + R_4 + R_5 + \frac{R_1}{R_2}(R_4 + R_5) + \frac{R_1}{R_3}(R_4 + R_5)}$$

wherein $R_1$–$R_5$ represent flow resistance values for each of the capillary element and the first, second, third and fourth channel segments, respectively, and $P_1$, $P_2$, $P_3$, and $P_5$ represent pressure values applied to the second end of the capillary element and to first, second and third ports fluidly coupled to said first, second, and third channel segments, respectively.

8. The method of claim 7 wherein the flow resistances of the first, second, and third channel segments and capillary element are determined based on lumped circuit analysis.

9. The method of claim 1 wherein the material transport system is selected to be an electrokinetic driving force.

10. The method of claim 9 wherein the electrokinetic driving force is selected to apply an electric field across at least one of the first, second and third channel segments.

11. The method of claim 10 wherein the driving force comprises an electric field applied concurrently across at least two of the first, second and third channel segments.

12. The method of claim 1 wherein the material transport system comprises a hybrid pressure-based and electrokinetic driving force.

13. The method of claim 12 wherein the hybrid driving force is selected to apply a positive or negative pressure to a point in at least one of the first, second or third channel segments and an electric field applied across a length of at least one of the first, second and third channel segments.

14. The method of claim 1 wherein the second analysis requirement comprises reaction time, and a first length of the first channel segment is provided such that reagents flowing through the first channel segment are present within the first channel segment for at least the reaction time.

15. The method of claim 1 wherein the second analysis requirement comprises separation time for constituent elements of fluid reagents under an applied electric field, and a first length of the first channel segment is provided such that reagents flowing through the first channel are present within the first channel segment for at least the separation time.

16. The method of claim 1 wherein the second analysis requirement comprises separation time for constituent components of a fluid material, and the first, second and third channel segments are chosen of a sufficient length such that the constituent elements in the fluid material transported through at least one of the channel segments are present within the one channel for the separation time, whereby the constituents separate.

17. The method of claim 1 wherein the microfluidic device comprises a planar body structure, the channel network being disposed within the planar body structure, the method further comprises configuring the first, second and third channel segments in the body structure of the microfluidic device such that the channel network has a footprint that is between about 0.25 cm$^2$ and about 200 cm$^2$.

18. The method of claim 1 wherein the microfluidic device comprises a planar body structure, the channel network being disposed within the planar body structure, the method further comprises configuring the first, second and third channel segments in the body structure of the microfluidic device such that the channel network has a footprint that is between about 0.25 cm$^2$ and about 6 cm$^2$.

19. The method of claim 1 wherein the microfluidic device comprises a planar body structure, the channel network being disposed within the planar body structure, the method further comprising providing at least one of the first, second and third channel segments with a depth of at least 10 µm.

20. The method of claim 1 wherein the at least first, second and third channel segments have cross-sectional dimensions of from about 0.1 µm to about 500 µm.

21. The method of claim 1 wherein the first channel segment comprises a reaction channel segment, and the second and third channel segments comprise reagent channels that are in fluid communication with the reaction channel segment.

22. The method of claim 21 wherein the first end of the capillary element is fluidly connected to the reaction channel segment at the first intersection.

23. The method of claim 1 further comprising selecting at least two or more second analysis requirements for the given analysis.

* * * * *